US 10,610,185 B2

United States Patent
Taguchi et al.

(10) Patent No.: US 10,610,185 B2
(45) Date of Patent: Apr. 7, 2020

(54) X-RAY CT APPARATUS INCLUDING PROCESSING CIRCUITRY TO PERFORM A METAL-ARTIFACT REDUCING PROCESS

(71) Applicants: Toshiba Medical Systems Corporation, Otawara-shi (JP); National Cancer Center, Chuo-ku (JP)

(72) Inventors: Hiroki Taguchi, Otawara (JP); Shinsuke Tsukagoshi, Nasushiobara (JP); Kotaro Sekiya, Bunkyo (JP); Hirofumi Kuno, Nagareyama (JP); Keiichi Nomura, Kashiwa (JP)

(73) Assignees: Canon Medical Systems Corporation, Otawara-shi (JP); National Cancer Center, Chuo-ku (JP)

( * ) Notice: Subject to any disclaimer, the term of this patent is extended or adjusted under 35 U.S.C. 154(b) by 213 days.

(21) Appl. No.: 15/470,338

(22) Filed: Mar. 27, 2017

(65) Prior Publication Data
US 2017/0273654 A1 Sep. 28, 2017

(30) Foreign Application Priority Data
Mar. 28, 2016 (JP) .................................. 2016-064474

(51) Int. Cl.
*A61B 6/00* (2006.01)
*A61B 6/03* (2006.01)
*A61B 6/14* (2006.01)

(52) U.S. Cl.
CPC ............ *A61B 6/5258* (2013.01); *A61B 6/032* (2013.01); *A61B 6/035* (2013.01); *A61B 6/14* (2013.01);
(Continued)

(58) Field of Classification Search
CPC ........... A61B 6/032; A61B 6/14; A61B 6/501; A61B 6/52; A61B 6/5205; A61B 6/5211;
(Continued)

(56) References Cited

U.S. PATENT DOCUMENTS 4,709,333 A * 11/1987 Crawford .............. G06T 11/005
378/4
6,094,467 A * 7/2000 Gayer .................. A61B 6/5258
378/4
(Continued)

FOREIGN PATENT DOCUMENTS

JP 2003-061948 A 3/2003
JP 4509497 7/2010
(Continued)

OTHER PUBLICATIONS

English translation of JP 2014-138911 A by Patent Translate on Feb. 8, 2020.*
(Continued)

*Primary Examiner* — Allen C. Ho
(74) *Attorney, Agent, or Firm* — Oblon, McClelland, Maier & Neustadt, L.L.P.

(57) ABSTRACT

An X-ray CT apparatus according to an embodiment includes processing circuitry. The processing circuitry is configured to detect X-rays that have passed through a subject by using a detector and to acquire projection data on a basis of a detection result. The processing circuitry is configured to obtain position information of a highly X-ray absorbent member in the body of the subject. The processing circuitry is configured to derive information about transmission paths of the X-rays in accordance with a processing effect of an artifact reducing process performed on the highly X-ray absorbent member, on the basis of the position information of the highly X-ray absorbent member.

20 Claims, 22 Drawing Sheets

(52) U.S. Cl.
CPC ............ *A61B 6/44* (2013.01); *A61B 6/4429* (2013.01); *A61B 6/4435* (2013.01); *A61B 6/461* (2013.01); *A61B 6/501* (2013.01); *A61B 6/52* (2013.01); *A61B 6/5211* (2013.01)

(58) Field of Classification Search
CPC ......... A61B 6/5258; A61B 6/035; A61B 6/44; A61B 6/4429; A61B 6/4435; A61B 6/4441
USPC ................................ 378/4, 38–40, 196–198
See application file for complete search history.

(56) References Cited

U.S. PATENT DOCUMENTS

| | | | | |
|---|---|---|---|---|
| 6,125,193 | A * | 9/2000 | Han | G06T 11/008 382/131 |
| 6,650,725 | B2 * | 11/2003 | Lutz | G06T 5/002 378/4 |
| 6,721,387 | B1 * | 4/2004 | Naidu | A61B 6/032 378/4 |
| 6,744,844 | B2 * | 6/2004 | Horiuchi | A61B 6/032 378/15 |
| 6,788,761 | B2 * | 9/2004 | Bijjani | G01N 23/046 378/19 |
| 6,816,571 | B2 * | 11/2004 | Bijjani | G01N 23/046 378/57 |
| 6,973,158 | B2 * | 12/2005 | Besson | A61B 6/032 378/16 |
| 7,023,951 | B2 * | 4/2006 | Man | A61B 6/00 378/4 |
| 7,039,156 | B2 * | 5/2006 | Arai | A61B 6/0478 378/22 |
| 7,099,428 | B2 * | 8/2006 | Clinthorne | A61B 6/14 378/17 |
| 7,103,135 | B2 * | 9/2006 | Koppe | G06T 11/005 378/15 |
| 7,206,440 | B2 * | 4/2007 | August | G06T 11/005 378/4 |
| 7,340,027 | B2 * | 3/2008 | Timmer | G06T 11/005 378/4 |
| 7,369,695 | B2 * | 5/2008 | Zettel | A61B 6/032 378/4 |
| 7,444,010 | B2 * | 10/2008 | De Man | G06T 11/005 378/8 |
| 7,548,604 | B2 * | 6/2009 | De Man | A61B 6/4447 378/17 |
| 7,574,025 | B2 * | 8/2009 | Feldman | A61C 1/084 382/128 |
| 7,623,905 | B2 * | 11/2009 | Haras | A61B 6/02 378/11 |
| 7,818,045 | B2 * | 10/2010 | Rietzel | A61B 6/032 345/419 |
| 8,023,767 | B1 * | 9/2011 | Ning | A61B 6/032 382/128 |
| 8,044,661 | B2 * | 10/2011 | Scholz | A61B 6/5258 324/300 |
| 8,160,199 | B2 * | 4/2012 | Rauch | A61B 6/032 378/210 |
| 8,259,896 | B2 * | 9/2012 | Kunze | G01N 23/046 378/4 |
| 8,280,135 | B2 * | 10/2012 | McCollough | A61B 6/032 378/4 |
| 8,410,448 | B2 * | 4/2013 | Forthmann | A61B 6/032 250/370.09 |
| 8,428,216 | B2 * | 4/2013 | Dennerlein | G06T 11/006 378/4 |
| 8,498,465 | B2 * | 7/2013 | Xing | G06T 11/005 382/131 |
| 8,503,750 | B2 * | 8/2013 | Benson | A61B 6/5258 378/4 |
| 8,582,855 | B2 * | 11/2013 | Koehler | A61B 6/5258 382/131 |
| 8,605,975 | B2 * | 12/2013 | Pan | G06T 11/006 382/130 |
| 8,633,445 | B2 * | 1/2014 | Star-Lack | A61B 6/032 250/363.02 |
| 8,699,812 | B2 * | 4/2014 | Hsieh | G06T 11/008 358/3.26 |
| 8,768,027 | B2 * | 7/2014 | Chen | G06T 11/005 378/4 |
| 8,768,032 | B2 * | 7/2014 | Basu | G06T 11/005 250/559.05 |
| 8,768,045 | B2 * | 7/2014 | Rohkohl | A61B 6/03 378/4 |
| 8,792,965 | B2 * | 7/2014 | Ning | A61B 6/032 600/427 |
| 8,891,885 | B2 * | 11/2014 | Kachelriess | A61B 6/00 382/232 |
| 8,989,343 | B2 * | 3/2015 | Arai | G06T 7/0012 378/20 |
| 9,058,658 | B2 * | 6/2015 | Li | G06T 7/0012 |
| 9,074,986 | B2 * | 7/2015 | Pal | G01N 23/046 |
| 9,202,296 | B2 * | 12/2015 | Yang | G06T 11/008 |
| 9,259,291 | B2 * | 2/2016 | Gantes | A61C 1/084 |
| 9,269,168 | B2 * | 2/2016 | Inglese | A61B 6/4241 |
| 9,275,454 | B2 * | 3/2016 | Grass | A61B 6/032 |
| 9,317,920 | B2 * | 4/2016 | Gluncic | G06K 9/00 |
| 9,349,198 | B2 * | 5/2016 | Claus | G06T 11/005 |
| 9,437,017 | B2 * | 9/2016 | Dong | G06T 11/008 |
| 9,443,295 | B2 * | 9/2016 | Dong | G06T 5/50 |
| 9,498,179 | B1 * | 11/2016 | Sen Sharma | A61B 6/5258 |
| 9,524,547 | B2 * | 12/2016 | Graumann | A61B 6/032 |
| 9,545,232 | B2 * | 1/2017 | Noordhoek | A61B 6/12 |
| 9,554,766 | B2 * | 1/2017 | Kyriakou | A61B 6/4085 |
| 9,610,055 | B2 * | 4/2017 | Taguchi | A61B 6/5205 |
| 9,662,081 | B2 * | 5/2017 | Maeda | A61B 6/032 |
| 9,706,973 | B2 * | 7/2017 | Takamatsu | A61B 6/482 |
| 9,730,663 | B2 * | 8/2017 | Koehler | G06T 7/149 |
| 9,757,075 | B2 * | 9/2017 | Mukumoto | A61B 6/03 |
| 9,818,383 | B2 * | 11/2017 | Shahbazmohamadi | G10D 9/02 |
| 9,865,060 | B2 * | 1/2018 | Mukumoto | A61B 6/5205 |
| 9,872,663 | B2 * | 1/2018 | Duewer | A61B 6/027 |
| 9,913,622 | B2 * | 3/2018 | Ida | A61B 6/5205 |
| 9,924,916 | B2 * | 3/2018 | Kato | A61B 6/4241 |
| 9,934,597 | B2 * | 4/2018 | Schildkraut | G06T 11/005 |
| 9,936,926 | B2 * | 4/2018 | Eronen | A61B 6/4035 |
| 9,953,441 | B2 * | 4/2018 | Han | G06T 11/008 |
| 9,968,318 | B2 * | 5/2018 | Kobayashi | A61B 6/03 |
| 10,013,779 | B2 * | 7/2018 | Silver | G06T 11/008 |
| 10,022,092 | B2 * | 7/2018 | Sakai | A61B 6/032 |
| 10,074,197 | B2 * | 9/2018 | Nitta | A61B 6/4241 |
| 10,092,266 | B2 * | 10/2018 | Pang | A61B 6/5205 |
| 10,111,626 | B2 * | 10/2018 | Goto | A61B 6/032 |
| 10,121,267 | B2 * | 11/2018 | Lin | G06T 11/008 |
| 10,130,320 | B2 * | 11/2018 | Saito | A61B 6/032 |
| 10,395,396 | B2 * | 8/2019 | Goto | G06T 11/008 |
| 10,453,198 | B2 * | 10/2019 | Manhart | A61B 6/5258 |
| 2011/0095197 | A1 | 4/2011 | Forthmann et al. | |
| 2017/0055935 | A1 * | 3/2017 | Takahashi | A61B 5/055 |

FOREIGN PATENT DOCUMENTS

| | | |
|---|---|---|
| JP | 4559113 | 10/2010 |
| JP | 4802079 | 10/2011 |
| JP | 2014-138911 A | 7/2014 |
| JP | 2005-323627 A | 11/2015 |
| WO | 2015/156125 A1 | 10/2015 |

OTHER PUBLICATIONS

English translation of JP 2005-323627 A by Patent Translate on Feb. 8, 2020.*

Yu-Bing Chang et al. "Metal Artifact Reduction Algorithm for Single Energy and Dual Energy CT Scans," IEEE Nuclear Science Symposium and Medical Imaging Conference Record (NSS/MIC), M17-47, 2012, pp. 4.

Pedro Augusto Gondim Teixeira et al. "Total hip prosthesis CT with single-energy projection-based metallic artifact reduction: impact

(56) References Cited

OTHER PUBLICATIONS on the visualization of specific periprosthetic soft tissue structures," Skeletal Radiol, DOI 10.1007/s00256-014-1923-5,Jun. 10, 2014, pp. 10.
Office Action dated Dec. 24, 2019 in corresponding Japanese Patent Application No. 2016-064474.

* cited by examiner

FIG.3
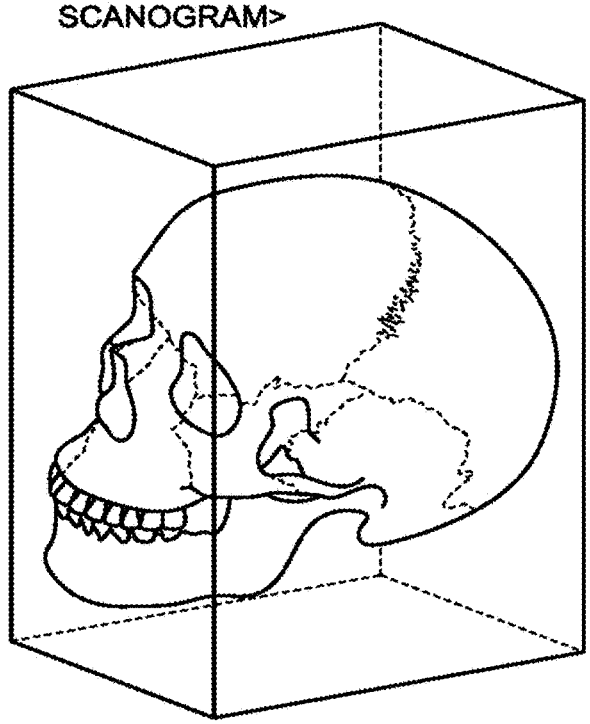
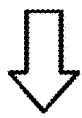
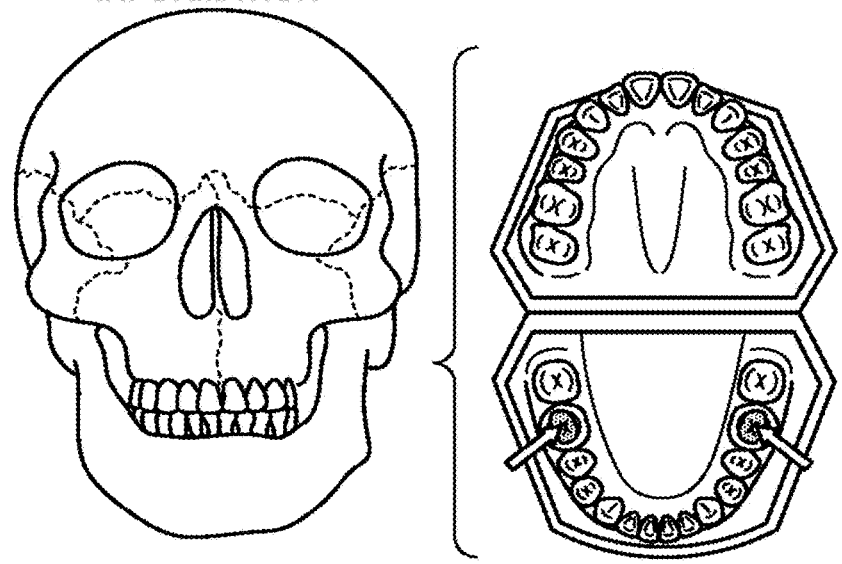

FIG.14
<DENTAL SYSTEMS>
ZSIGMONDY SYSTEM
| UPPER RIGHT 8 TO 1 (E TO A) | UPPER LEFT 1 TO 8 (A TO E) |
|---|---|
| LOWER RIGHT 8 TO 1 (E TO A) | LOWER LEFT 1 TO 8 (A TO E) |
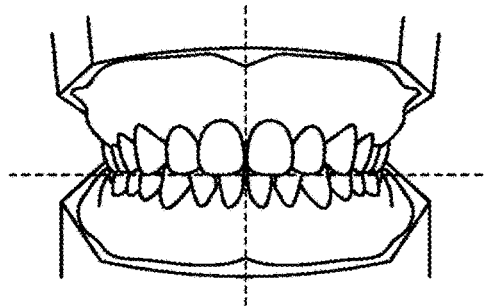
FDI SYSTEM
| 18 TO 11 (55 TO 51) | 21 TO 28 (61 TO 65) |
|---|---|
| 48 TO 41 (85 TO 81) | 31 TO 38 (71 TO 75) |
ADA SYSTEM
| 1 TO 8 (D1 TO D5) | 9 TO 16 (D6 TO D10) |
|---|---|
| 32 TO 25 (D20 TO D16) | 24 TO 17 (D15 TO D11) |

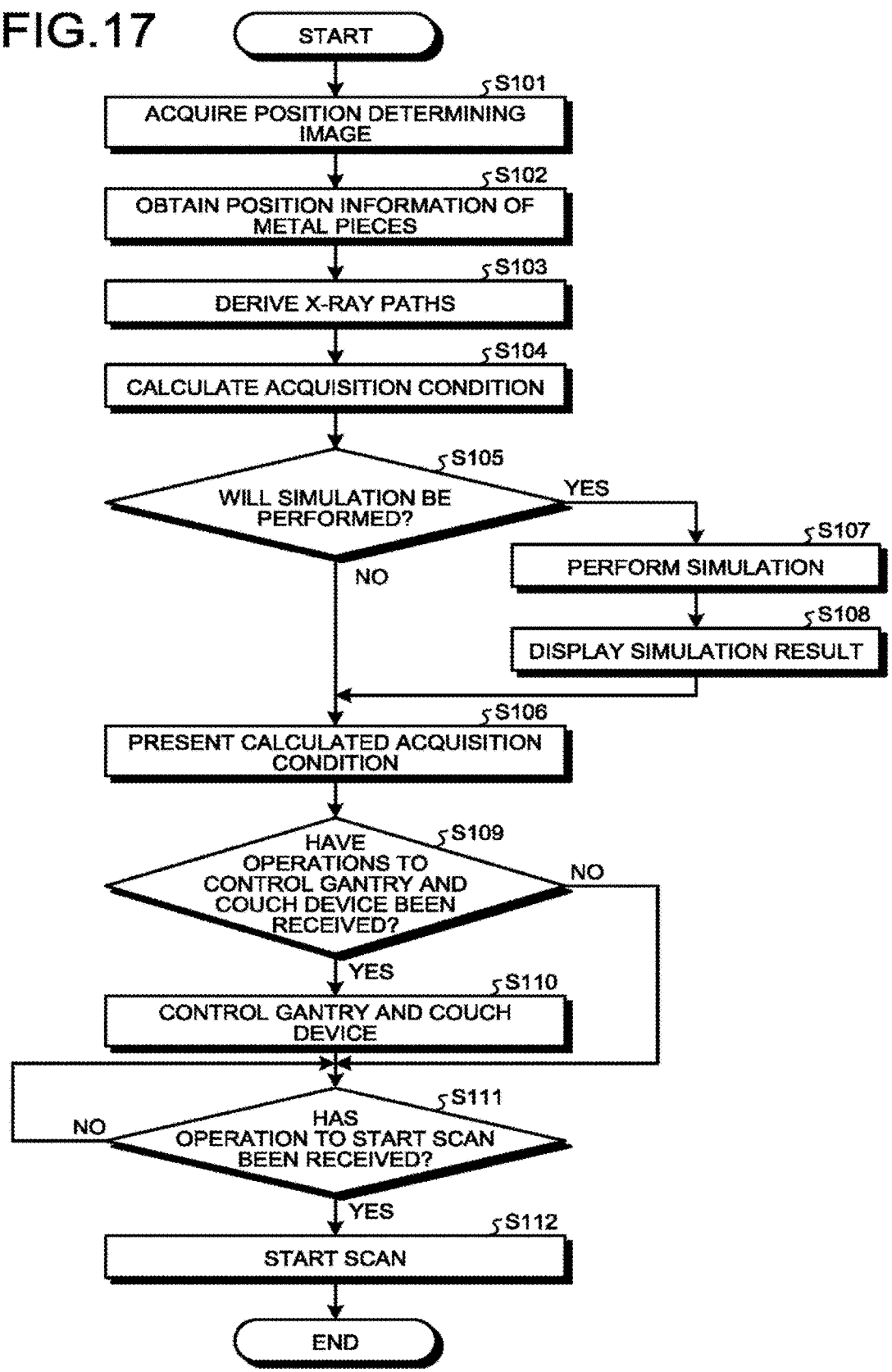

FIG.21
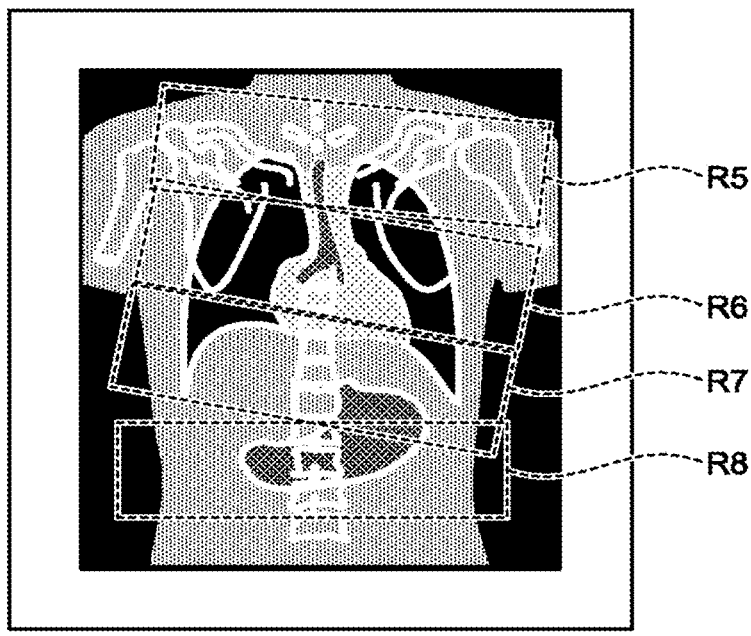
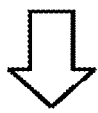
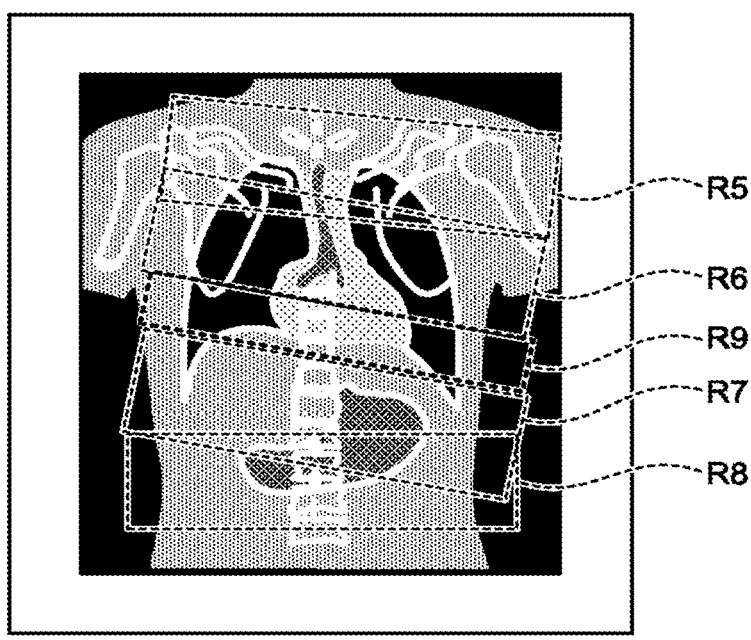

X-RAY CT APPARATUS INCLUDING PROCESSING CIRCUITRY TO PERFORM A METAL-ARTIFACT REDUCING PROCESS

CROSS-REFERENCE TO RELATED APPLICATIONS

This application is based upon and claims the benefit of priority from Japanese Patent Application No. 2016-064474, filed on Mar. 28, 2016; the entire contents of which are incorporated herein by reference.

FIELD

Embodiments described herein relate generally to an X-ray CT apparatus.

BACKGROUND

Conventionally, for an image taking process using an X-ray Computed Tomography (CT) apparatus, it is possible to perform a metal artifact reducing process to reduce artifacts caused by metal contained in the body of the subject. For example, the metal artifact reducing process is able to reduce artifacts caused by intracorporeal metal such as intraoral metal, intravascular metal, metal fixtures used for securing bones, other medical metal pieces, unwanted metallic intracorporeal matters, and the like and to improve the level of precision of diagnosing processes performed by using CT images. In the present example, the intraoral metal refers to metal that is placed to remain in the mouth for a dental treatment or the like, and examples also include dental implants. The intravascular metal refers to stents, coils, filters, and artificial valves, for example. Examples of the metal fixtures used for securing bones include plates, screws, wires, and the like. Further, examples of other medical metal pieces include clips, staples, implants, artificial joints, artificial bone heads, and pacemakers. Examples of the unwanted metallic intracorporeal matters include metal pieces and bullets.

BRIEF DESCRIPTION OF THE DRAWINGS

FIG. 3 is a drawing for explaining an example of a position information obtaining process performed by an obtaining function according to the first embodiment;

FIG. 14 is a drawing illustrating examples of dental systems received by input circuitry according to the first embodiment;

FIG. 17 is a flowchart illustrating a procedure in a process performed by the X-ray CT apparatus according to the first embodiment;

FIG. 21 is a drawing for explaining a scan range setting process according to the fourth embodiment;

DETAILED DESCRIPTION

According to an embodiment, an X-ray CT apparatus includes processing circuitry. The processing circuitry is configured to detect X-rays that have passed through a subject by using a detector and to acquire projection data on a basis of a detection result. The processing circuitry is configured to obtain position information of a highly X-ray absorbent member in a body of the subject. The processing circuitry is configured to derive information about transmission paths of the X-rays in accordance with a processing effect of an artifact reducing process performed on the highly X-ray absorbent member, on a basis of the position information of the highly X-ray absorbent member.

Exemplary embodiments of an X-ray Computed Tomography (CT) apparatus will be explained in detail below, with reference to the accompanying drawings. The embodiments described below are merely examples. Possible embodiments of the X-ray CT apparatus disclosed herein are not limited to the embodiments described below.

First Embodiment

Figure 1:
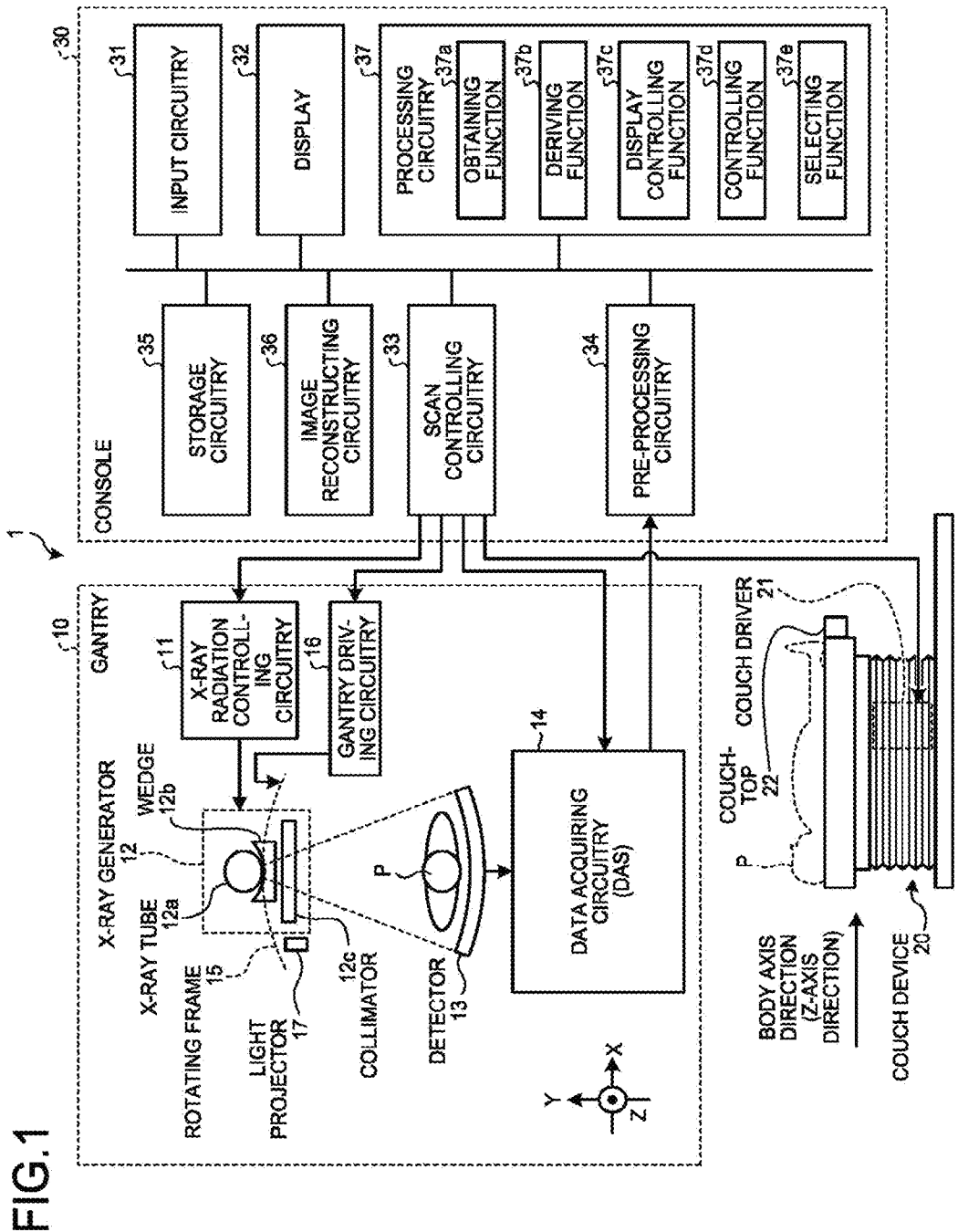
FIG. 1 is a diagram illustrating an exemplary configuration of an X-ray CT apparatus according to a first embodiment.

FIG. 1 is a diagram illustrating an exemplary configuration of an X-ray CT apparatus 1 according to a first embodiment. As illustrated in FIG. 1, the X-ray CT apparatus 1 according to the first embodiment includes a gantry 10, a couch device 20, and a console 30.

The gantry 10 is a device configured to radiate X-rays onto an examined subject P, to detect X-rays that have passed through the subject P, and to output a detection result to the console 30. The gantry 10 includes X-ray radiation controlling circuitry 11 an X-ray generator 12, a detector 13, data acquiring circuitry (a Data Acquisition System [DAS]) 14, a rotating frame 15, gantry driving circuitry 16, and a light projector 17.

The rotating frame 15 is an annular frame configured to support the X-ray generator 12 and the detector 13 so as to oppose each other while the subject P is interposed therebetween and configured to be rotated by the gantry driving circuitry 16 (explained later) at a high speed on a circular orbit centered on the subject P.

The X-ray radiation controlling circuitry 11 is configured to control a high voltage generator (not illustrated) so that a high voltage is supplied to an X-ray tube 12a. The X-ray tube 12a is configured to generate X-rays by using the high voltage supplied thereto from the high-voltage generator, under control of the X-ray radiation controlling circuitry 11. The X-ray radiation controlling circuitry 11 is configured to adjust the X-ray dose radiated onto the subject P, by adjusting the X-ray tube voltage and the X-ray tube current supplied to the X-ray tube 12a, under control of scan controlling circuitry 33 (explained later).

Further, the X-ray radiation controlling circuitry 11 is configured to perform a switching process on a wedge 12b. Further, by adjusting the opening degree of a collimator 12c, the X-ray radiation controlling circuitry 11 is configured to adjust the radiation range (a fan angle or a cone angle) of the X-rays. In the present embodiments, an arrangement is acceptable in which an operator manually switches among a plurality of types of wedges.

The X-ray generator 12 is a device configured to generate the X-rays and to radiate the generated X-rays onto the subject P. The X-ray generator 12 includes an X-ray tube 12a, the wedge 12b, and the collimator 12c.

The X-ray tube 12a is a vacuum tube configured to radiate an X-ray beam onto the subject P by using the high voltage supplied thereto by the high-voltage generating unit (not illustrated). The X-ray tube 12a radiates the X-ray beam onto the subject P, as the rotating frame 15 rotates. The X-ray tube 12a is configured to generate the X-ray beam that spreads with a fan angle or a cone angle. For example, under the control of the X-ray radiation controlling circuitry 11, the X-ray tube 12a is capable of continuously emitting X-rays in the entire surrounding of the subject P to realize a full reconstruction process and is capable of continuously emitting X-rays in an emission range (180 degrees+a fan angle) that enables a half reconstruction to realize a half reconstruction process.

Further, under the control of the X-ray radiation controlling circuitry 11, the X-ray tube 12a is capable of intermittently emitting X-rays (pulse X-rays) in positions (X-ray tube positions) set in advance. Further, the X-ray radiation controlling circuitry 11 is also capable of modulating the intensities of the X-rays emitted from the X-ray tube 12a. For example, the X-ray radiation controlling circuitry 11 increases the intensities of the X-rays emitted from the X-ray tube 12a in a specific X-ray tube position and decreases the intensities of the X-rays emitted from the X-ray tube 12a in a range other than the specific X-ray tube position.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the subject P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is a slit configured to narrow down the radiation range of the X-rays of which the X-ray dose has been adjusted by the wedge 12b, under the control of the X-ray radiation controlling circuitry 11 (explained later).

The gantry driving circuitry 16 is configured to cause the X-ray generator 12 and the detector 13 to revolve on the circular orbit centered on the subject P, by driving the rotating frame 15 to rotate. The light projector 17 is supported by the rotating frame 15 and is configured, under the control of the gantry driving circuitry 16, to irradiate a visible light beam (a laser) onto an image taking position where the X-rays are radiated onto the subject P. For example, the light projector 17 includes a slice plane light projector configured to irradiate a visible light beam onto a slice plane (an X-Y plane) and a median line light projector configured to irradiate a visible light beam onto a median line (a plane along the Z-axis) extending along the body axis. In this situation, the light projector 17 is also capable of irradiating a visible light beam onto a position deviating from the image taking position by a predetermined angle, in addition to the image taking position where the X-rays are radiated onto the subject P. The irradiation of the visible light beam by the light projector 17 is controlled under either continuous driving control or pulse driving control exercised by the gantry driving circuitry 16. In other words, the light projector 17 continuously irradiates the visible light beam under the continuous driving control and irradiates the visible light beam in the manner of a pulse at predetermined time intervals under the pulse driving control. Further, the light projector 17 is capable of shifting the light beam in the Z-axis direction, so as to realize a display in a position where the shape of the human body is easily recognized. Further, the light projector 17 is also capable of irradiating two laser beams and arbitrarily changing the position at which the two laser beams intersect each other. In other words, the operator is able to adjust the angle to irradiate a position where visual recognition is easier.

The detector 13 a two-dimensional array detector (a planar detector) configured to detect the X-rays that have passed through the subject P. In the detector 13, a plurality of rows of detecting elements are arranged along the body-axis direction of the subject P (i.e., the Z-axis direction in FIG. 2), while each row contains a plurality of X-ray detecting elements corresponding to a plurality of channels. More specifically, the detector 13 according to the first embodiment includes the X-ray detecting elements that are arranged in a large number of rows (e.g., 320 rows) along the body-axis direction of the subject P. For example, the detector 13 is capable of detecting X-rays that have passed through the subject P in a wide range such as a range including the lungs or the heart of the subject P.

The data acquiring circuitry 14 is configured with the DAS and is configured to acquire projection data from X-ray detection data detected by the X-ray detector 13. For example, the data acquiring circuitry 14 generates the projection data by performing an amplifying process, an Analog/Digital (A/D) converting process, a sensitivity correcting process among the channels, and/or the like on X-ray intensity distribution data detected by the detector 13 and further transmits the generated projection data to the console 30 (explained later). For example, when X-rays are continuously emitted from the X-ray tube 12a while the rotating frame 15 is rotating, the data acquiring circuitry 14 acquires a group of projection data corresponding to the entire surrounding (corresponding to 360 degrees). Further, the data acquiring circuitry 14 transmits the acquired pieces of projection data to the console 30 (explained later), while keeping the pieces of projection data in correspondence with the X-ray tube positions. The X-ray tube positions serve as information indicating projection directions of the pieces of projection data. As additional information, the sensitivity correcting process among the channels may be performed by pre-processing circuitry 34 (explained later).

The couch device 20 is a device on which the subject P is placed and includes a couch driver 21 and a couchtop 22, as illustrated in FIG. 1. The couch driver 21 is configured to move the subject P into the rotating frame 15 by moving the couchtop 22 in a Z-axis direction. The couchtop 22 is a board on which the subject P is placed. In the present example, the couch device 20 includes a slewing mechanism that turns while being centered on a predetermined axis (a slew center) that perpendicularly intersects the couchtop 22. Under the control of the scan controlling circuitry 33, for example, the slewing mechanism rotates either the couchtop 22 or a frame supporting the couchtop 22, while using the predetermined axis as the slew center. In this situation, the slewing mechanism includes a rotation sensor or the like configured to detect an angle (a slew angle) by which either the couchtop 22 or the frame supporting the couchtop 22 was rotated. On the basis of the slew angle detected in this manner, it is possible to calculate the amount by which the couchtop 22 was moved in the left-and-right direction by the slewing.

For example, the gantry 10 performs a helical scan by which the subject P is helically scanned by causing the rotating frame 15 to rotate while the couchtop 22 is being moved. In another example, the gantry 10 performs a conventional scan by which the subject P is scanned on a circular orbit by causing the rotating frame 15 to rotate, while the position of the subject P is being fixed after the couchtop 22 is moved. In yet another example, the gantry 10 implements a step-and-shoot method by which the conventional scan is performed in multiple scan areas, by moving the position of the couchtop 22 at regular intervals.

Further, the gantry 10 includes a tilting mechanism that turns while being centered on a predetermined axis (a tilt center) extending in a horizontal direction. Under the control of the scan controlling circuitry 33, for example, the tilting mechanism tilts the gantry, while using the predetermined axis as the tilt center. Further, the gantry 10 includes a slewing mechanism that turns while being centered on the predetermined axis (the slew center) extending along the vertical direction. Under the control of the scan controlling circuitry 33, for example, the slewing mechanism causes the gantry 10 to rotate while using the predetermined axis as the slew center. The tilting mechanism and the slewing mechanism include a rotation sensor or the like configured to detect the angle (the tilt angle) by which the gantry 10 was tilted and the angle (the slew angle) by which the gantry 10 was rotated. On the basis of the tilt angle and the slew angle detected in this manner, it is possible to calculate the amount by which the gantry 10 was moved by the tiling in the front-and-back direction and the amount by which the gantry 10 was moved by the slewing in the left-and-right direction.

The console 30 is a device configured to receive operations performed by the operator on the X-ray CT apparatus 1 and also configured to reconstruct CT image data by using the projection data acquired by the gantry 10. As illustrated in FIG. 1, the console 30 includes input circuitry 31, a display 32, the scan controlling circuitry 33, the pre-processing circuitry 34, storage circuitry 35, image reconstructing circuitry 36, and processing circuitry 37.

The input circuitry 31 includes a mouse, a keyboard, a trackball, a switch, a button, a joystick, and/or the like used by the operator of the X-ray CT apparatus 1 to input various types of instructions and various types of settings. The input circuitry 31 is configured to transfer information about the instructions and the settings received from the operator to the processing circuitry 37. For example, the input circuitry 31 receives, from the operator, an image taking condition for the CT image data, a reconstructing condition used when the CT image data is reconstructed, an image processing condition applied to the CT image data, and the like. Further, the input circuitry 31 also receives a designation operation to designate a site or a predetermined region such as a region of interest within an image.

The display 32 is a monitor referenced by the operator and is configured to display a CT image generated from the CT image data for the operator and to display a Graphical User Interface (GUI) used for receiving the various types of instructions and the various types of settings from the operator via the input circuitry 31, under control of the processing circuitry 37. Further, the display 32 is also configured to display information about transmission paths (which hereinafter may be referred to as "paths") of X-rays. The information about the X-ray paths will be explained in detail later.

Under the control of the processing circuitry 37, the scan controlling circuitry 33 is configured to control the projection data acquiring process performed by the gantry 10, by controlling operations of the X-ray radiation controlling circuitry 11, the gantry driving circuitry 16, the data acquiring circuitry 14, and the couch driver 21. More specifically, the scan controlling circuitry 33 is configured to control projection data acquiring processes during an image taking process to acquire a position determining image (a scanogram image) and during a main image taking process (a scan) to acquire an image used for a diagnosis purpose. In the present example, the X-ray CT apparatus 1 according to the first embodiment is configured so as to be able to take a two-dimensional scanogram image and a three-dimensional scanogram image.

For example, by continuously taking images while moving the couchtop 22 at a constant speed and having the X-ray tube 12a fixed in the position corresponding to 0 degrees (a straight-on position of the subject), the scan controlling circuitry 33 takes the two-dimensional scanogram image. Alternatively, by intermittently moving the couchtop 22 while the X-ray tube 12a is fixed in the position corresponding to 0 degrees, the scan controlling circuitry 33 may take the two-dimensional scanogram image by repeatedly taking images intermittently in synchronization with the moving of the couchtop. In the present example, the scan controlling circuitry 33 is capable of taking the position determining image, not only from the straight-on direction of the subject P, but also from any arbitrary direction (e.g., a lateral direction).

Further, by acquiring the projection data corresponding to the entire surrounding of the subject P during a scanogram image taking process, the scan controlling circuitry 33 takes the three-dimensional scanogram image. For example, the scan controlling circuitry 33 acquires the projection data corresponding to the entire surrounding of the subject, by performing either a helical scan or a non-helical scan. In this situation, the scan controlling circuitry 33 performs the helical scan or the non-helical scan on a wide range such as the entire chest, the entire abdomen, the entire upper body, or the entire body of the subject, by using an X-ray dose smaller than that used in the main image taking process. To perform the non-helical scan, for example, a scan is performed by implementing the step-and-shoot method described above. An X-ray CT apparatus configured to take the three-dimensional scanogram image described above will be explained as an example of the X-ray CT apparatus 1 according to the present embodiments; however, possible embodiments are not limited to this example. The present disclosure is also applicable to X-ray CT apparatuses configured to take only two-dimensional scanogram images.

When the scan controlling circuitry 33 has acquired the projection data corresponding to the entire surrounding of the subject in this manner, the image reconstructing circuitry 36 (explained later) is able to reconstruct three-dimensional CT image data (volume data). It is therefore possible to generate the position determining image from an arbitrary direction, by using the reconstructed volume data. In this situation, whether the position determining image is taken two-dimensionally or three-dimensionally may arbitrarily be selected by the operator or may be configured in advance in accordance with specifics of the medical examination to be performed.

Further, by controlling the gantry driving circuitry 16, the scan controlling circuitry 33 controls the tilting mechanism and the slewing mechanism included in the gantry 10. For example, the scan controlling circuitry 33 tilts the gantry 10 by a predetermined tilt angle, by controlling the tilting mechanism included in the gantry 10, on the basis of the information about the X-ray paths derived by the processing circuitry 37 (explained later). As another example, the scan controlling circuitry 33 causes the gantry 10 to rotate by a predetermined slew angle, by controlling the slewing mechanism included in the gantry 10 on the basis of the information about the X-ray paths. Further, the scan controlling circuitry 33 controls the slewing mechanism included in the couch device 20, by controlling the couch driver 21. For example, the scan controlling circuitry 33 causes either the couchtop 22 or the frame supporting the couchtop 22 to rotate by a predetermined slew angle, by controlling the slewing mechanism included in the couch device 20 on the basis of the information about the X-ray paths. In the present example, the scan controlling circuitry 33 is capable of controlling the tilting mechanism and the slewing mechanism included in the gantry 10 and the slewing mechanism included in the couch device 20 each alone. Further, the scan controlling circuitry 33 is also capable of controlling these mechanisms in conjunction with one another.

The pre-processing circuitry 34 is configured to generate corrected projection data by performing a logarithmic converting process as well as correcting processes such as an offset correcting process, a sensitivity correcting process, a beam hardening correcting process, and the like, on the projection data generated by the data acquiring circuitry 14. More specifically, the pre-processing circuitry 34 generates pieces of corrected projection data both for the projection data of the position determining image and for the projection data acquired by performing the main image taking process that were generated by the data acquiring circuitry 14 and further stores the pieces of corrected projection data into the storage circuitry 35.

The storage circuitry 35 is configured to store therein the projection data generated by the pre-processing circuitry 34. More specifically, the storage circuitry 35 stores therein the projection data of the position determining image and the projection data for the diagnosis purpose acquired by performing the main image taking process that were generated by the pre-processing circuitry 34. Further, the storage circuitry 35 is configured to store therein the CT image generated by the image reconstructing circuitry 36 (explained later) and the like. Further, the storage circuitry 35 is configured to store therein a processing result obtained by the processing circuitry 37 (explained later), as appropriate.

The image reconstructing circuitry 36 is configured to reconstruct the CT image data by using the projection data stored in the storage circuitry 35. More specifically, the image reconstructing circuitry 36 reconstructs pieces of CT image data both from the projection data of the position determining image and the projection data of the image for the diagnosis purpose. In this situation, any of various methods can be used as the reconstructing method. For example, a back projection process may be used. Further, examples of the back projection process include a back projection process using a Filtered Back Projection (FBP) method. Alternatively, the image reconstructing circuitry 36 may reconstruct the CT image data by using a successive approximation method.

Further, the image reconstructing circuitry 36 is configured to perform a metal artifact reducing process. For example, the image reconstructing circuitry 36 reduces metal artifacts by performing an image reconstructing process to which a successive approximation reconstructing method is applied. In one example, the image reconstructing circuitry 36 reduces the metal artifacts, by extracting a metal region contained in projection data (a sinogram) and eliminating the extracted metal region by performing an interpolating process. In other words, the image reconstructing circuitry 36 reconstructs the CT image data in which metal artifacts are reduced. Further, the image reconstructing circuitry 36 is configured to generate various types of CT images by performing various types of image processing processes on the CT image data. After that, the image reconstructing circuitry 36 stores the reconstructed CT image data and the CT images generated by performing the various types of image processing processes, into the storage circuitry 35.

The processing circuitry 37 is configured to exercise overall control of the X-ray CT apparatus 1 by controlling operations of the gantry 10, the couch device 20, and the console 30. More specifically, the processing circuitry 37 is configured to control a CT scan performed by the gantry 10, by controlling the scan controlling circuitry 33. Also, the processing circuitry 37 is configured to control the image reconstructing process and the image generating process performed by the console 30, by controlling the image reconstructing circuitry 36. Further, the processing circuitry 37 is configured to exercise control so that the display 32 displays various types of CT images stored in the storage circuitry 35.

Further, as illustrated in FIG. 1, the processing circuitry 37 is configured to execute an obtaining function 37a, a deriving function 37b, a display controlling function 37c, a controlling function 37d, and a selecting function 37e. In this situation, for example, processing functions executed by the constituent elements of the processing circuitry 37 illustrated in FIG. 1, namely the functions such as the obtaining function 37a, the deriving function 37b, the display controlling function 37c, the controlling function 37d, and the selecting function 37e are recorded in the storage circuitry 35 in the form of computer-executable programs. The processing circuitry 37 is a processor configured to realize the functions corresponding to the computer programs (hereinafter, "programs"), by reading the programs from the storage circuitry 35 and executing the read programs. In other words, the processing circuitry 37 that has read the programs has the functions illustrated within the processing circuitry 37 in FIG. 1.

The processing circuitry 37 described in the present embodiments is an example of the processing circuitry set forth in the claims. The light projector 17 is an example of the light projector set forth in the claims. The display 32 is an example of the display set forth in the claims.

The term "processor" used in the explanation above denotes, for example, a circuit such as a Central Processing Unit (CPU), a Graphics Processing Unit (GPU), an Application Specific Integrated Circuit (ASIC), or a programmable logic device (e.g., a Simple Programmable Logic Device [SPLD], a Complex Programmable Logic Device [CPLD], or a Field Programmable Gate Array (FPGA)). Each of the processors realizes the function thereof by reading a program stored in the storage circuitry and executing the read program. Alternatively, it is also acceptable to directly incorporate the program into the circuit of each of the processors, instead of having the programs stored in the storage circuitry. In that situation, each of the processors realizes the function thereof by reading the program incorporated in the circuit thereof and executing the read program. The processors according to the present embodiments each do not necessarily have to be configured as a single circuit. It is also acceptable to structure a single processor by combining together a plurality of independent circuits so as to realize the functions thereof.

An overall configuration of the X-ray CT apparatus 1 according to the first embodiment has thus been explained. The X-ray CT apparatus 1 according to the first embodiment configured as described above makes it possible to further reduce the metal artifacts. As explained above, in X-ray CT apparatuses, a metal artifact reducing process is performed for the purpose of reducing artifacts caused by intracorporeal metal such as intraoral metal, intravascular metal, metal fixtures used for securing bones, other medical metal pieces, and unwanted metallic intracorporeal matters. In this situation, metal artifact reducing processes performed by the X-ray CT apparatus 1 exhibit various processing effects depending on positions of intracorporeal metal pieces. More specifically, the processing effect of a metal artifact reducing process is lowered, when a plurality of metal pieces are included in transmission paths (paths) of the X-rays that are used when the X-rays are radiated onto a subject.

The intraoral metal refers to metal that is placed to remain in the mouth for a dental treatment or the like, and examples also include dental implants. The intravascular metal refers to stents, coils, filters, and artificial valves, for example. Examples of the metal fixtures used for securing bones include plates, screws, wires, and the like. Further, examples of other medical metal pieces include clips, staples, implants, artificial joints, artificial bone heads, and pacemakers. Examples of the unwanted metallic intracorporeal matters include metal pieces and bullets.

The intracorporeal metal explained above such as intraoral metal, stents, coils, and the like are placed to remain in the bodies of subjects as a result of various treatments. When CT image data is acquired from a subject who has intracorporeal metal, the metal artifact reducing process described above is performed. However, when a plurality of metal pieces are included in the X-ray paths that are used when the CT image data is acquired, the processing effect of the metal artifact reducing process is lowered, and an impact may be made on diagnosing processes. In one example, intraoral metal is metal placed to remain in the mouth as a result of a dental treatment and is an example of intracorporeal metal that is found in the oral cavity of a large number of subjects. Further, as for intraoral metal, it is often true with many subjects that two or more intraoral metal pieces are placed to remain in the oral cavity. Accordingly, when CT image data is acquired from the inside of the oral cavity of those subjects, there is a high possibility that two or more metal pieces are included in the X-ray paths. For example, when CT image data is acquired for the purpose of observing the degree of infiltration of a tumor (e.g., tongue cancer) in the oral cavity, if two or more intraoral metal pieces are included in the X-ray paths, the effect of the metal artifact reducing process is lowered. There is also a possibility that it may be difficult to accurately assess the degree of infiltration of the tumor in the oral cavity. To cope with this situation, the X-ray CT apparatus 1 according to the first embodiment makes it possible to further reduce such metal artifacts, by using the control exercised by the processing circuitry 37 explained in detail below.

More specifically, the X-ray CT apparatus 1 according to the first embodiment is configured to set X-ray paths so as to optimize the processing effect of the metal artifact reducing process on the basis of position information of metal pieces contained in the body of a subject. For example, the X-ray CT apparatus 1 sets the X-ray paths in such a manner that the quantity of metal pieces positioned on the X-ray paths is one or smaller. Also, the X-ray CT apparatus 1 sets the X-ray paths so as to minimize the quantity of metal pieces positioned on the X-ray paths. In another example, the X-ray CT apparatus 1 sets the X-ray paths so as to maximize the distance between metal pieces positioned on the X-ray paths. In the following sections, these processes will be explained one by one. In the embodiments described below, processes will be explained in detail, while using the example of acquiring CT image data from the inside of the oral cavity.

Figure 2:
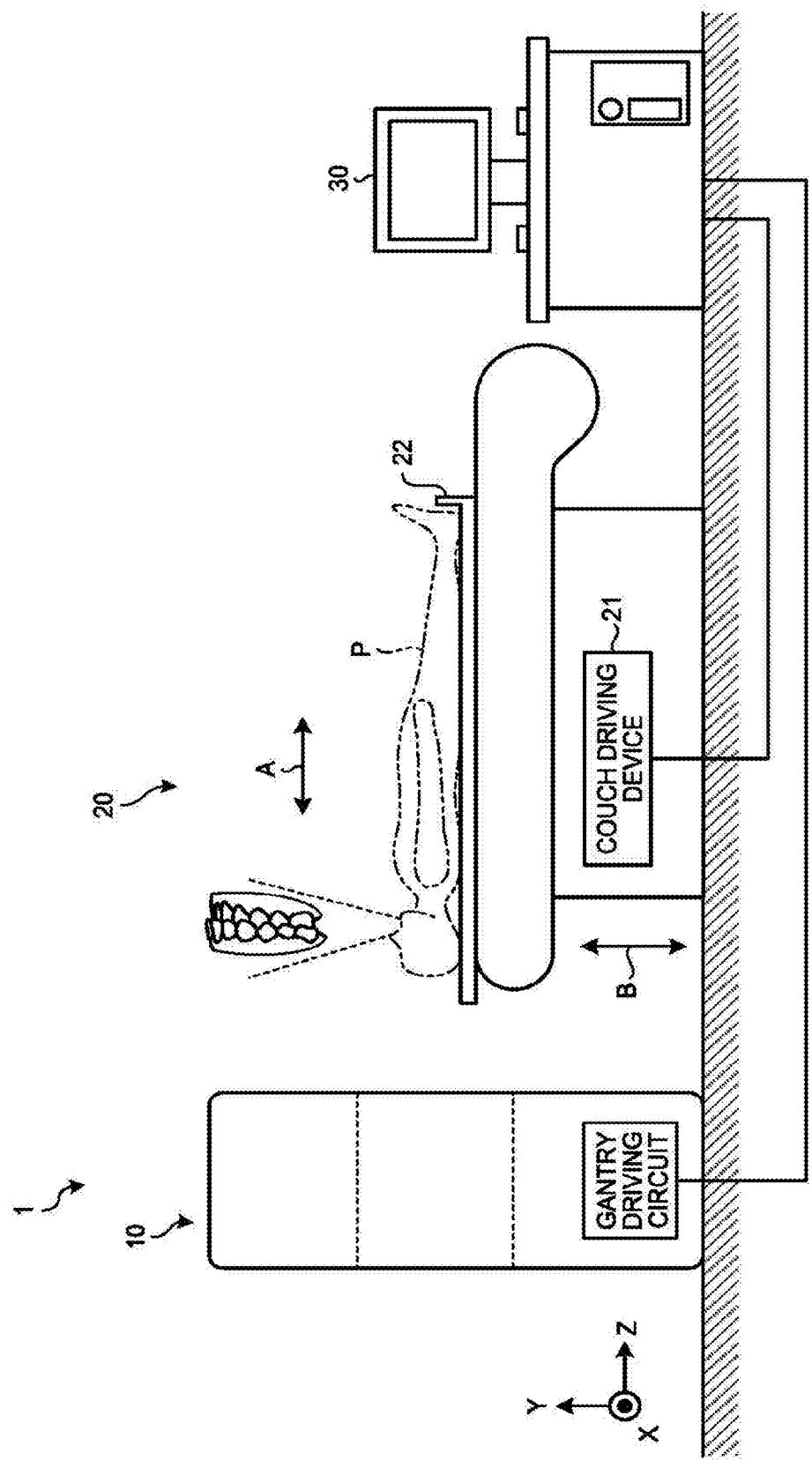
FIG. 2 is a drawing for explaining a CT image data acquiring process performed inside the oral cavity according to the first embodiment.

First, an example of acquiring CT image data from the inside of the oral cavity will be explained, with reference to FIG. 2. FIG. 2 is a drawing for explaining a CT image data acquiring process performed inside the oral cavity according to the first embodiment. For example, when CT image data is acquired from the inside of the oral cavity, the subject P lies down on the couchtop 22, as illustrated in FIG. 2. Further, under the control of the scan controlling circuitry 33 included in the console 30, the couchtop 22 is brought out, so that the gantry 10 radiates X-rays and detects X-rays that have passed through the inside of the oral cavity of the subject P. In this situation, as illustrated in FIG. 2, the occlusal plane (the plane on which the teeth on the upper jaw and the teeth on the lower jaw occlude) of the subject P is approximately parallel to the X-Y plane used in the CT image data acquiring process. Accordingly, there is a high possibility that a plurality of intraoral metal pieces placed on teeth of the subject may be included in the X-ray paths. The X-ray CT apparatus 1 according to the first embodiment is configured to set the X-ray paths used in the CT image data acquiring process performed on the inside of the oral cavity, so as to optimize the processing effect of the metal artifact reducing process, by using processes performed by the processing circuitry 37 explained in detail below.

The obtaining function 37a according to the first embodiment is configured to obtain position information of a highly X-ray absorbent members in the body of the subject. More specifically, the obtaining function 37a obtains three-dimensional position information of an intracorporeal metal piece in the body of the subject. For example, the obtaining function 37a obtains the position (e.g., coordinate information) of an intraoral metal piece placed to remain on a tooth of the subject, within a three-dimensional space in which the CT image data is acquired. In one example, the obtaining function 37a extracts a metal region on the basis of absorption of X-rays observed when a position determining image (a scanogram image) is acquired and further obtains position information of the extracted metal region.

FIG. 3 is a drawing for explaining an example of the position information obtaining process performed by the obtaining function 37a according to the first embodiment. As illustrated in FIG. 3, the obtaining function 37a obtains CT values in the voxels of a three-dimensional position determining image acquired by implementing three-dimensional scanography and further extracts a group of voxels of which the obtained CT values exhibit values corresponding to metal. After that, the obtaining function 37a obtains the coordinates of the extracted group of voxels as the metal regions. Accordingly, for example, as illustrated in the lower section of FIG. 3, the obtaining function 37a obtains position information within the three-dimensional position determining image with respect to each of the intraoral metal pieces placed on the tooth identified as "lower right 6" and the tooth identified as "lower left 6". In other words, the obtaining function 37a obtains the coordinate information of the metal regions within the three-dimensional space in which the CT image data is acquired.

Figure 4:
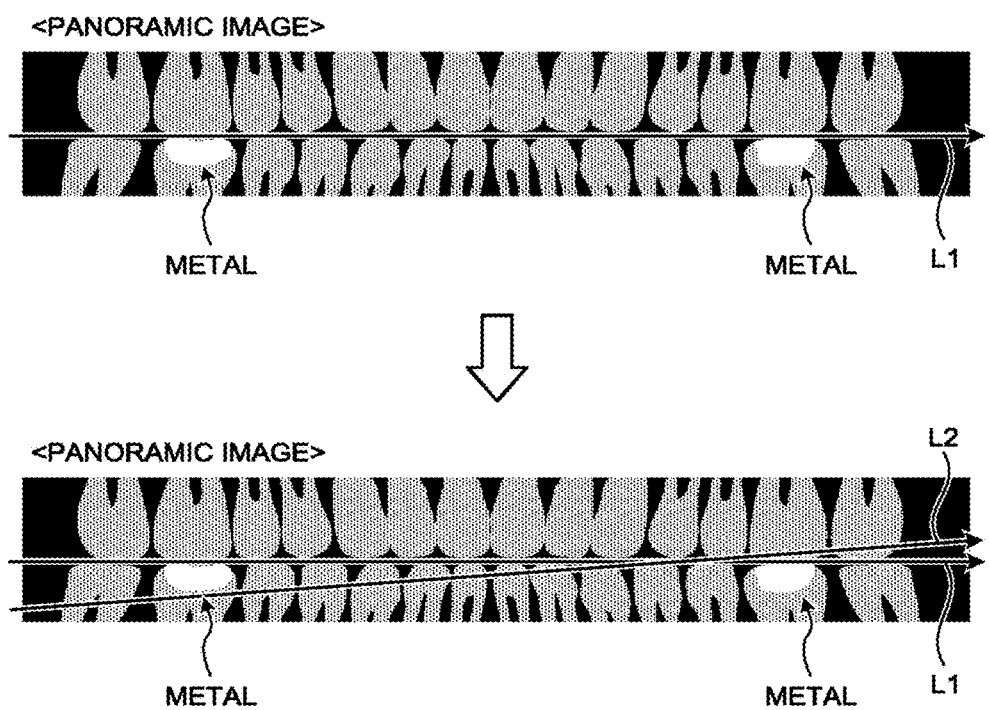
FIG. 4 is a drawing for explaining an example of an X-ray path deriving process performed by a deriving function according to the first embodiment.

The deriving function 37b is configured to derive information about the transmission paths (the paths) of the X-rays in accordance with the processing effect of the metal artifact reducing process performed on the highly X-ray absorbent members, on the basis of the position information of the highly X-ray absorbent members. More specifically, the deriving function 37b sets the X-ray paths so as to optimize the processing effect of the metal artifact reducing process. For example, the deriving function 37b derives information about X-ray paths that keep the quantity of metal pieces positioned on the X-ray paths one or smaller. FIG. 4 is a drawing for explaining an example of the X-ray path deriving process performed by the deriving function 37b according to the first embodiment. FIG. 4 illustrates panoramic images of rows of teeth serving as position determining images acquired three-dimensionally. The panoramic images illustrated in FIG. 4 are images rendering the rows of teeth on the upper and the lower jaws in developed-view pictures in a panoramic manner. Further, in each of the panoramic images in FIG. 4, the upper rows of teeth are the teeth on the upper jaw, whereas the lower rows of teeth are the teeth on the lower jaw. In other words, in each of the panoramic images in FIG. 4, the height direction corresponds to the Z-axis direction, whereas the width direction corresponds to the X-axis direction.

For example, as illustrated in the drawing in the upper section of FIG. 4, intraoral metal pieces are placed on the tooth identified as "lower right 6" and the tooth identified as "lower left 6". When a set of X-ray paths is established as indicated by the straight line L1, two metal pieces are included in the straight line L1 (the set of X-ray paths). Accordingly, CT image data acquired in this state has a lower processing effect in the metal artifact reducing process. To cope with this situation, the deriving function 37b derives a set of paths so as to keep the quantity of metal pieces included in the X-ray paths one or smaller, on the basis of the position information (the coordinate information) of the metal pieces (the metal piece placed on the tooth identified as "lower right 6" and the metal piece placed on the tooth identified as "lower left 6") obtained by the obtaining function 37a.

For example, the deriving function 37b derives the straight line L2 illustrated in the lower section of FIG. 4, as a set of X-ray paths to be used in a main scan performed on the subject illustrated in FIG. 4. In other words, as the set of X-ray paths, the deriving function 37b derives the straight line L2 so that neither of the metal pieces (the metal piece placed on the tooth identified as "lower right 6" and the metal piece placed on the tooth identified as "lower left 6") is included in the set of paths. For example, the deriving function 37b derives the straight line L2, by identifying the metal regions in a sinogram and calculating a set of paths so that no paths are positioned in the identified region. In the present example, although FIG. 4 illustrates the situation where the derived set of paths includes neither of the metal pieces; however, possible embodiments are not limited to this example. For instance, it is acceptable to derive a set of paths including one of the metal pieces. When the main scan is performed by using the derived set of X-ray paths, it is possible to achieve a sufficient level of the processing effect in the metal artifact reducing process, even if one of the metal pieces is included in the set of X-ray paths.

In this situation, the X-ray CT apparatus 1 is able to perform a volume scan by radiating the X-rays onto the subject by using a cone beam having a predetermined cone angle (for example, 15 degrees at maximum). In other words, the X-rays radiated in the cone beam include X-rays having various angles. However, when a scan is performed by using such a cone beam, each of the pieces of data based on the X-rays radiated in the cone beam is converted to a piece of data arranged on a plane fitted to a predetermined plane (e.g., the X-Y plane). Accordingly, all the X-ray paths extend parallel to each other. For example, even when the X-rays are radiated onto the subject illustrated in FIG. 4 by using a cone beam, the X-ray paths are arranged in such a manner that planes positioned parallel to the plane indicated by the straight line L1 are arranged in the Z-axis direction.

Accordingly, even in the situation where the X-rays are radiated by using a cone beam, the deriving function 37b derives X-ray paths in accordance with the processing effect of the metal artifact reducing process in the same manner.

The controlling function 37d is configured to set an acquisition condition used for acquiring projection data, on the basis of the information about the X-ray paths. More specifically, the controlling function 37d sets the acquisition condition used for acquiring the projection data in the main scan, by using the X-ray paths derived by the deriving function 37b. For example, the controlling function 37d calculates the acquisition condition to change the X-ray paths that are currently set (the X-ray paths used when the position determining image was acquired) into the derived paths. In one example, the controlling function 37d calculates an acquisition condition (e.g., the set of paths is tilted by "5 degrees" with respect to the X-Y plane, while using the Y-direction as the axis) to change the set of X-ray paths indicated by the straight line L1 into the set of paths indicated by the straight line L2.

Figure 5A:
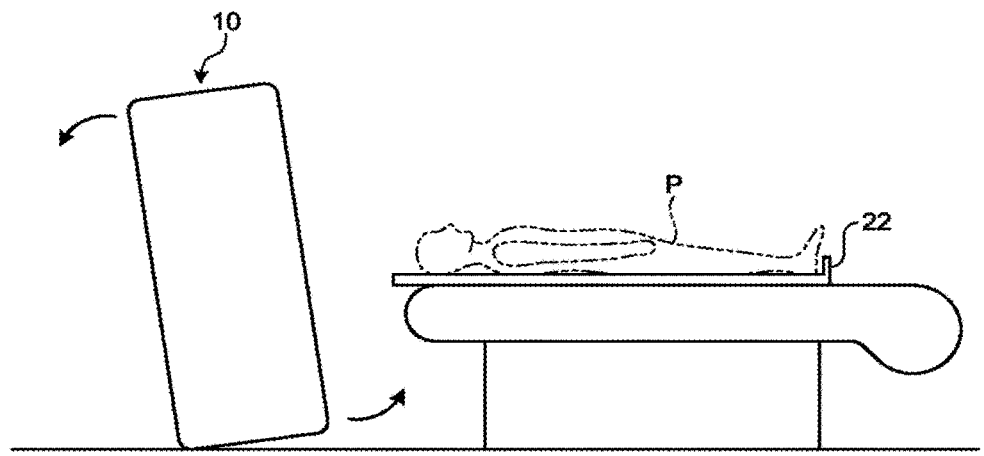
FIG. 5A is a drawing illustrating an example of control exercised by a controlling function according to the first embodiment.
Figure 5B:
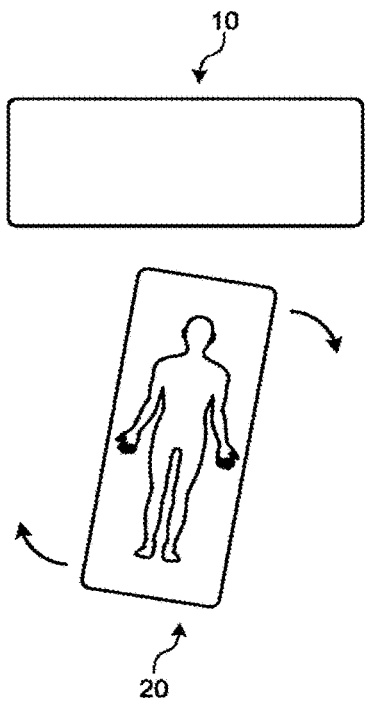
FIG. 5B is a drawing illustrating another example of the control exercised by the controlling function according to the first embodiment.
Figure 5C:
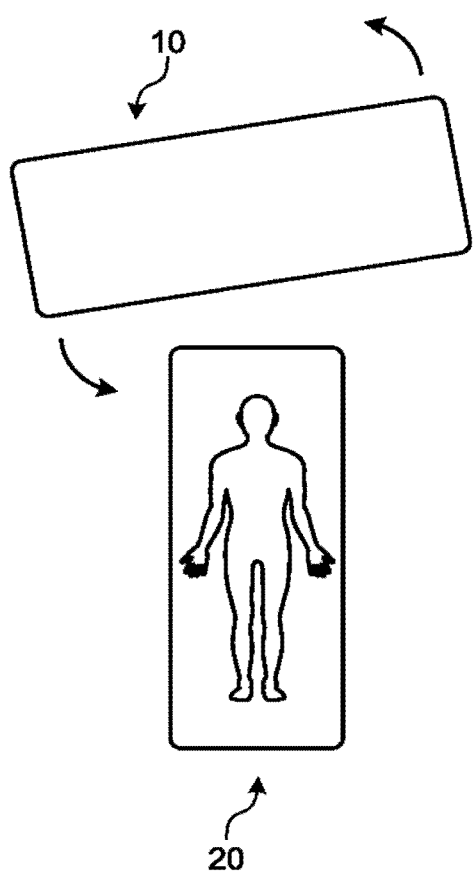
FIG. 5C is a drawing illustrating yet another example of the control exercised by the controlling function according to the first embodiment.

Further, the controlling function 37d controls the gantry 10 and the couch device 20, so as to meet the calculated acquisition condition. For example, the controlling function 37d controls at least one selected from among the following: the tilt angle of the gantry 10; the rotation angle (the slew angle) of the gantry 10; and the rotation angle (the slew angle) of the couch device 20. FIGS. 5A to 5C are drawings illustrating examples of the control exercised by the controlling function 37d according to the first embodiment. In the present example, FIG. 5A is a drawing illustrating an example of the control exercised on the tilt angle of the gantry 10 by the controlling function 37d. FIG. 5B is a drawing illustrating an example of the control exercised on the slew angle of the couch device 20 by the controlling function 37d. FIG. 5C is a drawing illustrating an example of the control exercised on the slew angle of the gantry 10 by the controlling function 37d.

For example, as illustrated in FIG. 5A, the controlling function 37d tilts the gantry 10 by a predetermined tilt angle. In one example, the controlling function 37d tilts the gantry 10 by the predetermined tilt angle, when the X-ray paths are tilted at the predetermined angle with respect to the X-Y plane while the X-direction is used as the axis. Further, for example, as illustrated in FIG. 5B, the controlling function 37d rotates the couch device 20 by a predetermined slew angle. In one example, the controlling function 37d rotates the couch device 20 by the predetermined slew angle, when the X-ray paths are tilted at the predetermined angle with respect to the X-Y plane while the Y-direction is used as the axis. Further, as illustrated in FIG. 5C, the controlling function 37d rotates the gantry 10 by a predetermined slew angle. In one example, the controlling function 37d rotates the gantry 10 by the predetermined slew angle, when the X-ray paths are tilted at the predetermined angle with respect to the X-Y plane while the Y-direction is used as the axis. In this situation, the controlling function 37d exercises these types of control individually or in a combined manner in accordance with the acquisition condition used for changing the X-ray paths.

Figure 6A:
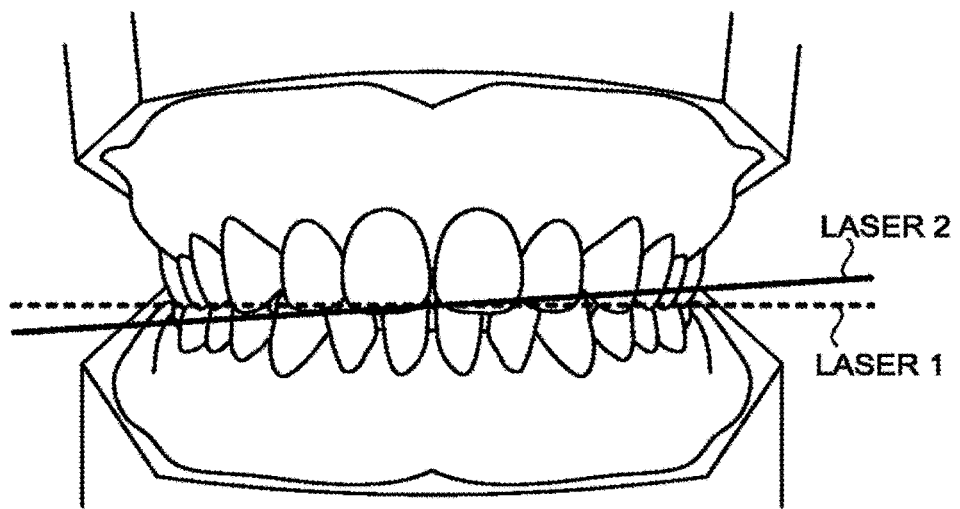
FIG. 6A is a drawing illustrating an example of a light projector control exercised by the controlling function according to the first embodiment.
Figure 6B:
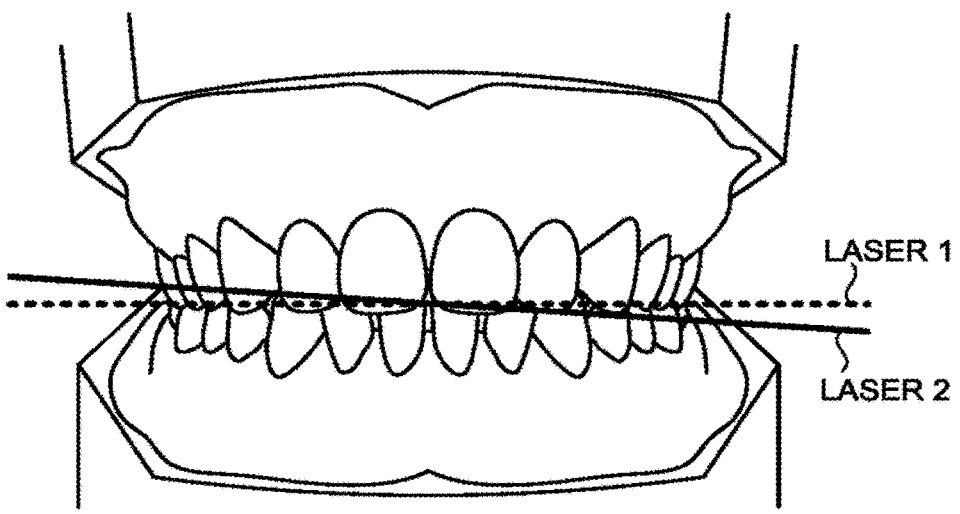
FIG. 6B is a drawing illustrating another example of the light projector control exercised by the controlling function according to the first embodiment.

Further, the controlling function 37d is capable of exercising control so as to present the information about the X-ray paths derived by the deriving function 37b. For example, the controlling function 37d controls the light projector 17 so as to project light to a position on the body surface of the subject corresponding to the X-ray paths. FIGS. 6A and 6B are drawing illustrating examples of the control exercised on the light projector 17 by the controlling function 37d according to the first embodiment. FIGS. 6A and 6B illustrate the manner in which a teeth part of the subject is irradiated with laser beams from the light projector 17. For example, as illustrated in FIG. 6A, the controlling function 37d controls the light projector 17 so that the teeth part of the subject are irradiated with a laser beam 1 indicating the current set of X-ray paths (e.g., the straight line L1 in FIG. 4) and a laser beam 2 indicating the set of X-ray paths derived by the deriving function 37b (e.g., the straight line L2 in FIG. 4). By irradiating the laser beam indicating the set of X-ray paths onto the body surface of the subject in this manner, the user is able to recognize, at a glance, the status of the set of X-ray paths in accordance with the processing effect of the metal artifact reducing process. For example, when X-ray paths are changed by using the slewing mechanism of the gantry 10 and/or the couch device 20, the laser beam 2 comes into alignment with the occlusal plane with which the laser beam 1 is aligned.

In the description above, the example is explained in which the X-ray paths are changed by using the tilting mechanism and the slewing mechanism of the gantry 10 and the slewing mechanism of the couch device 20; however, possible embodiments are not limited to this example. For instance, it is also acceptable to change the X-ray paths into the derived paths, by changing the posture of the subject, for example. It is acceptable to change the X-ray paths by tilting the face of the subject by "5 degrees", for example. In that situation, for example, as illustrated in FIG. 6B, the controlling function 37d exercises control so that the laser beam 2 with which the occlusal plane of the subject is to be aligned is emitted. In other words, when the subject is moved, instead of the gantry 10 and/or the couch device 20 being moved, the controlling function 37d exercises control so that the laser beam 2 is emitted while being tilted in the direction opposite to the direction used when the apparatus is moved. By tilting the face of the subject so that the occlusal plane of the subject is aligned with the laser beam 2, the operator who operates the X-ray CT apparatus 1 is able to change the X-ray paths.

Figure 7:
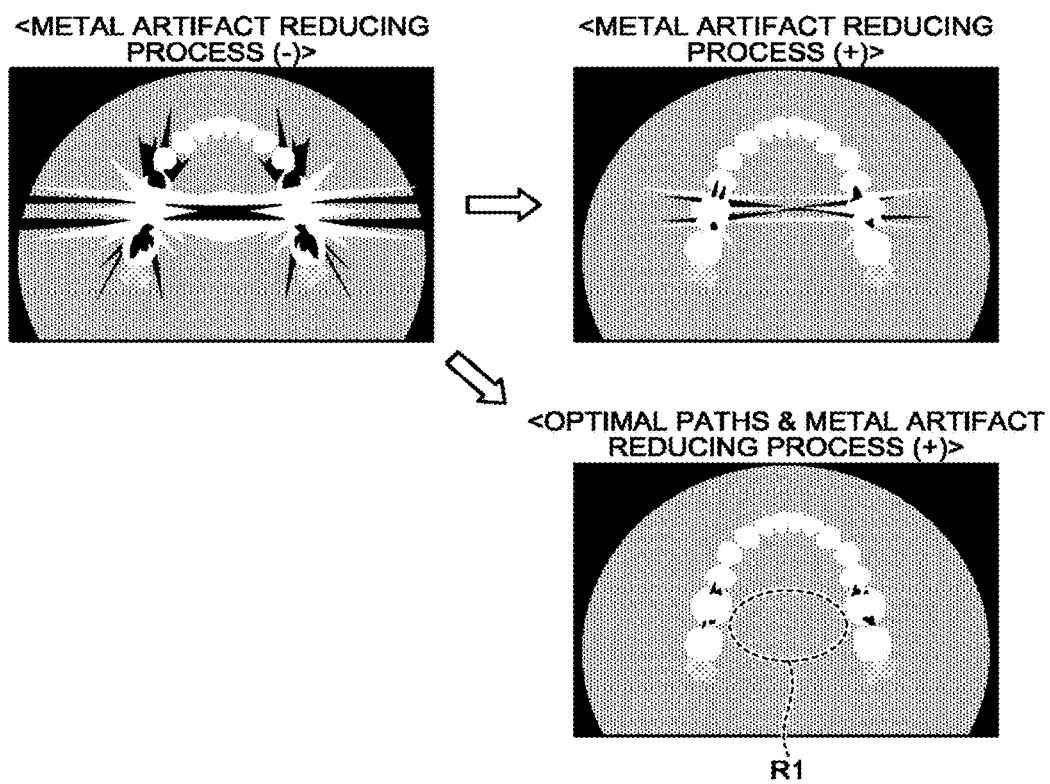
FIG. 7 is a drawing illustrating an example of a metal artifact reducing process performed by the X-ray CT apparatus according to the first embodiment.

As explained above, the X-ray CT apparatus 1 is configured to set the paths so that the quantity of metal pieces positioned on the X-ray paths is one or smaller, for the purpose of further reducing the metal artifacts. With this arrangement, it is possible to improve the processing effect of the metal artifact reducing process. FIG. 7 is a drawing illustrating an example of the metal artifact reducing process performed by the X-ray CT apparatus 1 according to the first embodiment. FIG. 7 illustrates a CT image ("metal artifact reducing process (−)" in the drawing) obtained when no metal artifact reducing process is performed; a CT image ("metal artifact reducing process (+)" in the drawing) obtained when a metal artifact reducing process is performed; and a CT image ("optimal paths & metal artifact reducing process (+)" in the drawing) obtained when the X-ray paths are changed to fit the straight line L2 in the lower section of FIG. 4, and also, a metal artifact reducing process is performed.

For example, when no metal artifact reducing process is performed, artifacts occurring from the metal pieces placed on the teeth make a significant impact on the CT image. Further, for example, when the metal artifact reducing process is performed, although the artifacts occurring from the metal pieces placed on the teeth are reduced compared to the example without the process, significant artifacts remain primarily in the region connecting together the teeth on which the metal pieces are placed. Accordingly, when the site to be observed is positioned between metal pieces, there is a possibility that it may not be possible to accurately perform a diagnosing process due to the impact of the artifacts. In contrast, when the X-ray paths are changed, and also, a metal artifact reducing process is performed, almost all the artifacts in the CT image are eliminated, including those positioned between the metal pieces, as illustrated in the lower right section of FIG. 7. Consequently, even when the site to be observed is positioned in the region R1 in FIG. 7, for example, the viewer is able to perform a diagnosing process with a high level of precision.

Figure 8:
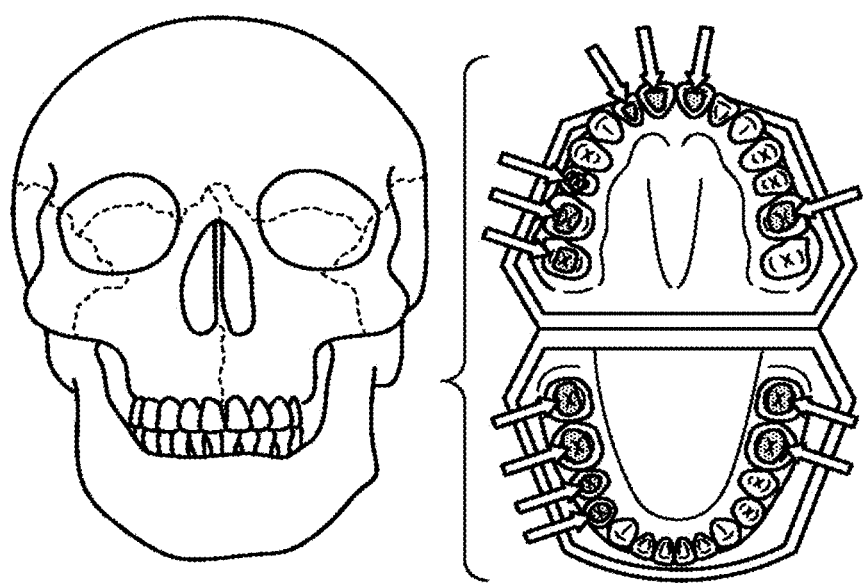
FIG. 8 is a drawing illustrating an example of intraoral metal pieces according to the first embodiment.

In the embodiment described above, the example is explained in which the quantity of intraoral metal pieces is two, and the operator is able to set the optimal paths (the paths arranged so that the quantity of metal pieces positioned thereon is one or smaller). However, for example, there may be some other situations where the quantity of intraoral metal pieces is larger, depending on situations with dental treatments. For example, as illustrated in FIG. 8, when an intraoral metal piece is placed on each of the teeth identified as "upper right 1", "upper right 2", "upper right 5 to 7", "upper left 1", "upper left 6", "lower right 4 to 7", "lower left 6" and "lower left 7", there may be some situations where it is difficult to set optimal paths because a large part of the position determining image is accounted for by the metal pieces. FIG. 8 is a drawing illustrating an example of the intraoral metal pieces according to the first embodiment.

Figure 9A:
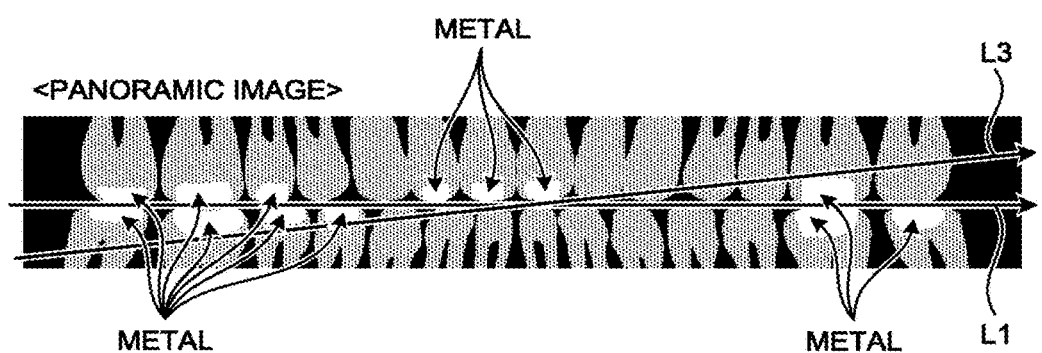
FIG. 9A is a drawing illustrating another example of the X-ray path deriving process performed by the deriving function according to the first embodiment.

In that situation, for example, the deriving function 37b derives such a set of paths that minimizes the overlapping of the metal pieces, in view of the entire region of the oral cavity. In other words, the deriving function 37b sets the X-ray paths so as to minimize the quantity of metal pieces positioned on the X-ray paths. FIG. 9A is a drawing illustrating another example of the X-ray path deriving process performed by the deriving function 37b according to the first embodiment. FIG. 9A illustrates a panoramic image of rows of teeth in a position determining image acquired three-dimensionally from the subject illustrated in FIG. 8. For example, the deriving function 37b derives the straight line L3 in FIG. 9A as the X-ray paths (i.e., the paths obtained by tilting the X-ray paths at "10 degrees" with respect to the X-Y plane, while using the Y-direction as the axis). In this situation, when the straight line L3 illustrated in FIG. 9A is used as the paths, even when the X-rays are radiated by using a cone beam, at most two metal pieces are included. In other words, the deriving function 37b derives the set of paths so as to minimize the quantity of metal pieces positioned on mutually the same path, when a plurality of planes (a plurality of paths) positioned parallel to the straight line L3 are arranged in the Z-axis direction.

Figure 9B:
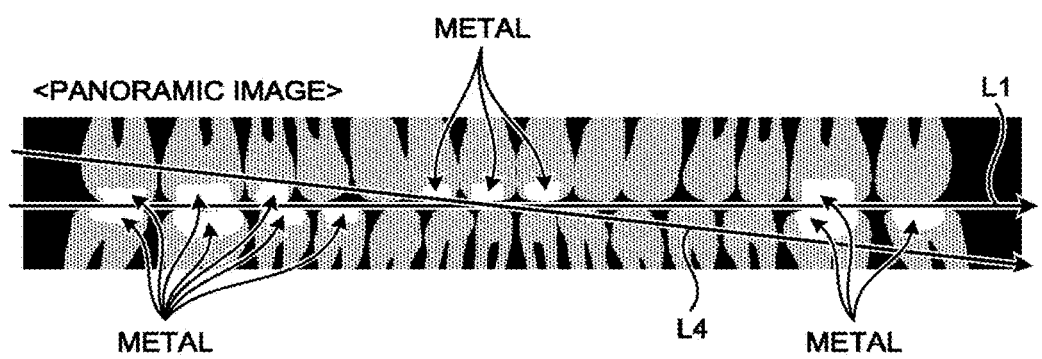
FIG. 9B is a drawing illustrating yet another example of the X-ray path deriving process performed by the deriving function according to the first embodiment.

The controlling function 37d sets an acquisition condition so that a main scan is performed by using the paths derived by the deriving function 37b. In this situation, for example, when it is expected to be difficult to tilt the X-ray paths at "10 degrees" with respect to the X-Y plane, in consideration of the subject's convenience or for some reasons related to the medical examination, the deriving function 37b derives a set of paths from a different direction. FIG. 9B is a drawing illustrating yet another example of the X-ray path deriving process performed by the deriving function 37b according to the first embodiment. FIG. 9B illustrates a panoramic image of rows of teeth in a position determining image acquired three-dimensionally from the subject illustrated in FIG. 8. For example, the deriving function 37b derives the straight line L4 in FIG. 9B as the X-ray paths (i.e., the paths obtained by tilting the X-ray paths in the opposite direction at "6 degrees" with respect to the X-Y plane, while using the Y-direction as the axis). In this situation, as explained above with reference to FIG. 9A, by using the set of paths in the opposite direction, the deriving function 37b derives such a set of paths that minimizes the overlapping of the metal pieces in view of the entire region of the oral cavity.

Figure 10:
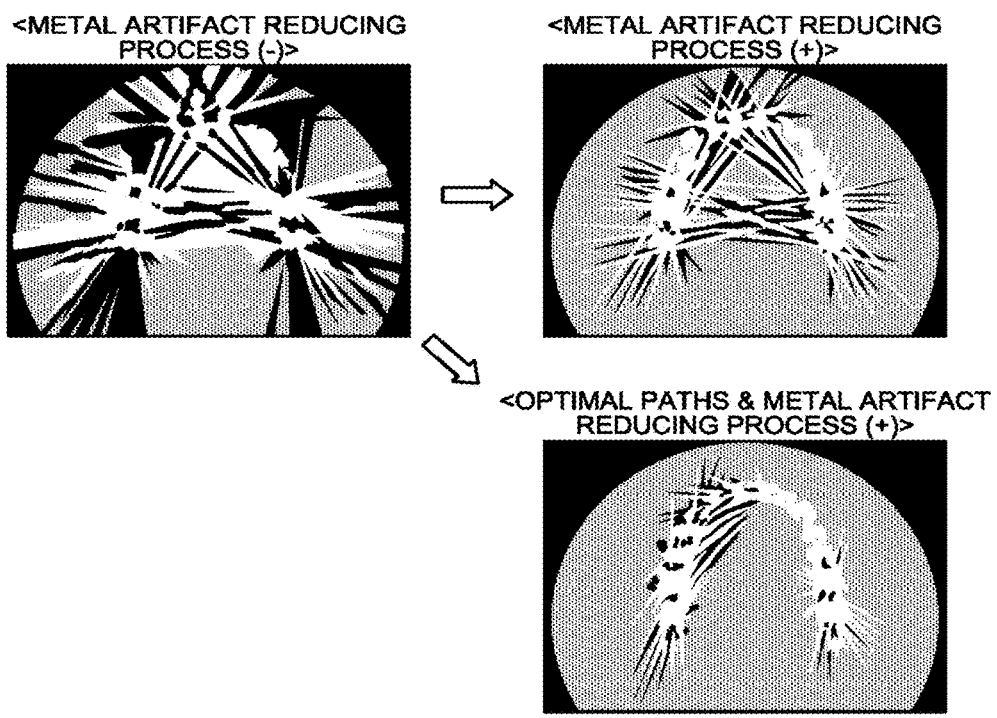
FIG. 10 is a drawing illustrating another example of the metal artifact reducing process performed by the X-ray CT apparatus according to the first embodiment.

As explained above, even when it is expected to be difficult to set an optimal set of paths because metal pieces in a large quantity are included in the target site from which the CT image data is to be acquired, the X-ray CT apparatus 1 derives the set of paths that minimizes the overlapping of the metal pieces and exercises control so that the main scan is performed by using the derived set of paths. With this configuration, it is possible to improve the processing effect of the metal artifact reducing process. FIG. 10 is a drawing illustrating another example of the metal artifact reducing process performed by the X-ray CT apparatus 1 according to the first embodiment. FIG. 10 illustrates a CT image ("metal artifact reducing process (−)" in the drawing) obtained when no metal artifact reducing process is performed; a CT image ("metal artifact reducing process (+)" in the drawing) obtained when a metal artifact reducing process is performed; and a CT image ("optimal paths & metal artifact reducing process (+)" in the drawing) obtained when the X-ray paths are changed to fit the straight line L3 in FIG. 9A, and also, a metal artifact reducing process is performed.

For example, when no metal artifact reducing process is performed, the artifacts occurring from the metal pieces in a large quantity placed on the teeth make a significant impact on the entire CT image. It is therefore difficult to use the CT image for a diagnosis purpose. Further, for example, when the metal artifact reducing process is performed, although the artifacts occurring from the metal pieces placed on the teeth are reduced compared to the example without the process, artifacts occur among the large number of teeth on which the metal pieces are placed. It is therefore difficult to use the CT image for a diagnosis purpose. In contrast, when the X-ray paths are changed, and also, the metal artifact reducing process is performed, the artifacts in the CT image are eliminated except for those on the left side, as illustrated in the lower right section of FIG. 10. Consequently, when the site to be observed is positioned on the right side, for example, the viewer is able to perform a diagnosing process with a high level of precision.

Further, the X-ray CT apparatus 1 according to the first embodiment is capable of setting X-ray paths so as to maximize the distance between the metal pieces positioned on the X-ray paths. In some situations, metal artifact reducing processes may not achieve a high processing effect when the metal pieces are positioned closed to one another, due to the nature of the process. To cope with this situation, the X-ray CT apparatus 1 according to the first embodiment is also capable of maximizing the effect of the metal artifact reducing process, by setting such a set of paths that maximizes the distance between the metal pieces positioned on mutually the same set of paths. In that situation, the deriving function 37b derives the set of paths that maximizes the distance between the metal pieces on the basis of the position information of the metal pieces obtained by the obtaining function 37a. For example, when there are two or more sets of paths that each minimize the quantity of metal pieces positioned on mutually the same set of paths, the deriving function 37b calculates the distance between the metal pieces on each set of paths and derives such a set of paths that maximizes the calculated distance as the X-ray paths to be used in the main scan.

Figure 11:
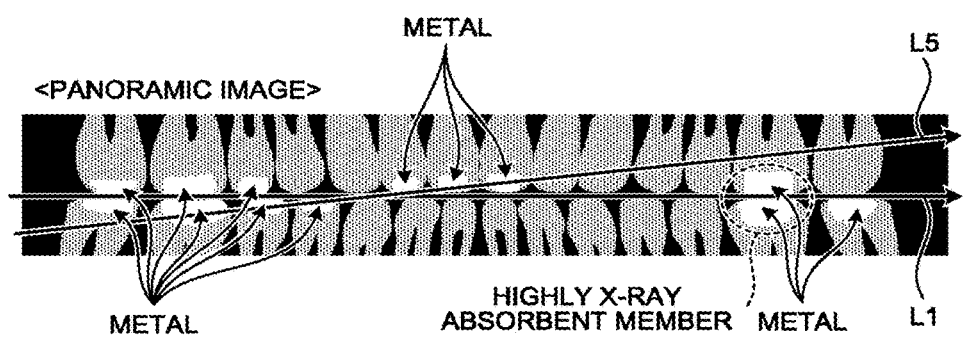
FIG. 11 is a drawing illustrating yet another example of the X-ray path deriving process performed by the deriving function according to the first embodiment.

In the example above, the example is explained in which such a set of paths that minimizes the overlapping of the metal pieces on mutually the same set of paths is derived. However, the X-ray CT apparatus 1 is also capable of setting paths in accordance with degrees of X-ray absorption. More specifically, the deriving function 37*b* derives a set of paths obtained by eliminating, from a previous set of X-ray paths, at least the most highly X-ray absorbent member among the plurality of highly X-ray absorbent members in the body of the subject. FIG. 11 is a drawing illustrating yet another example of the X-ray path deriving process performed by the deriving function 37*b* according to the first embodiment. FIG. 11 illustrates a panoramic image of rows of teeth in a position determining image acquired three-dimensionally from the subject illustrated in FIG. 8. For example, the deriving function 37*b* extracts the position of the most highly X-ray absorbent metal piece, from among the plurality of metal pieces, on the basis of degrees of X-ray absorption (e.g., CT values) obtained by the obtaining function 37*a*. After that, as illustrated in FIG. 11, the deriving function 37*b* derives a set of paths so that at least the most highly X-ray absorbent metal piece (the "highly absorbent member", in the drawing) is not included in the paths. In other words, the deriving function 37*b* derives the set of paths extending along the straight line L5 illustrated in FIG. 11, by identifying the region of the highly absorbent member from the sinogram and calculating a set of paths so that no paths are positioned in the identified region. The controlling function 37*d* controls the gantry 10 and the couch device 20 so that the X-ray paths used in the main scan extend along the straight line L5.

The examples of deriving the X-ray paths on the basis of the position information of the metal pieces have thus been explained. Further, the X-ray CT apparatus 1 is also capable of deriving X-ray paths in consideration of the position of an arbitrary region, in addition to the position information of the metal pieces described above. More specifically, during a metal artifact reducing process, the deriving function 37*b* derives information about X-ray paths so as to reduce metal artifacts in a region of interest within the CT image data reconstructed from the projection data. For example, the deriving function 37*b* derives the X-ray paths on the basis of the position information of the metal pieces and position information of the region of interest, in such a manner that no artifact occurs in the region of interest designated by the operator.

Figure 12A:
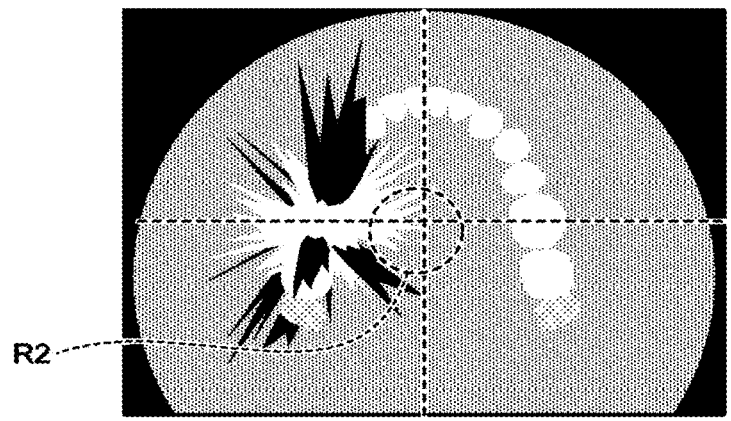
FIG. 12A is a drawing illustrating an example of a region-of-interest setting process according to the first embodiment.

FIG. 12A is a drawing illustrating an example of a region-of-interest setting process according to the first embodiment. FIG. 12A illustrates an axial cross-sectional image of the oral cavity generated from CT image data of a position determining image acquired three-dimensionally. For example, by referring to the axial cross-sectional image illustrated in FIG. 12A, the operator sets a region of interest R2 as a region that he/she wishes to evaluate in particular.

Figure 12B:
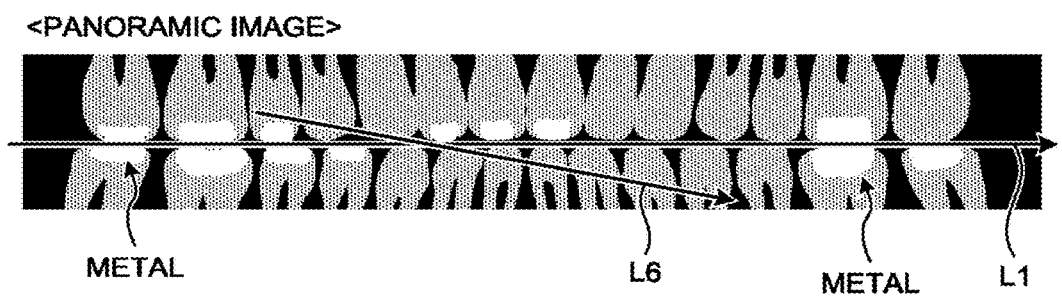
FIG. 12B is a drawing illustrating yet another example of the X-ray path deriving process performed by the deriving function according to the first embodiment.

The deriving function 37*b* derives X-ray paths by using the region of interest R2 set by the operator and the position information of the metal pieces obtained by the obtaining function 37*a*. In other words, the deriving function 37*b* derives a set of X-ray paths so that no metal artifact occurs in the region of interest R2. FIG. 12B is a drawing illustrating yet another example of the X-ray path deriving process performed by the deriving function 37*b* according to the first embodiment. For example, the deriving function 37*b* derives a set of paths as indicated by the straight line L6 in FIG. 12B. In one example, the deriving function 37*b* determines which metal pieces cause the metal artifact occurring in the region of interest R2 designated in FIG. 12A and derives the straight line L6 as the set of paths, so that the determined metal pieces are not included in mutually the same set of paths. In other words, the deriving function 37*b* derives the set of X-ray paths so that the group of metal pieces illustrated on the left side in FIG. 12A (the group of metal pieces illustrated on the right side in FIG. 12B) is not positioned on mutually the same set of paths. After that, for example, the controlling function 37*d* controls the gantry 10 and the couch device 20 so that the X-ray paths used in the main scan extend along the straight line L6.

Figure 12C:
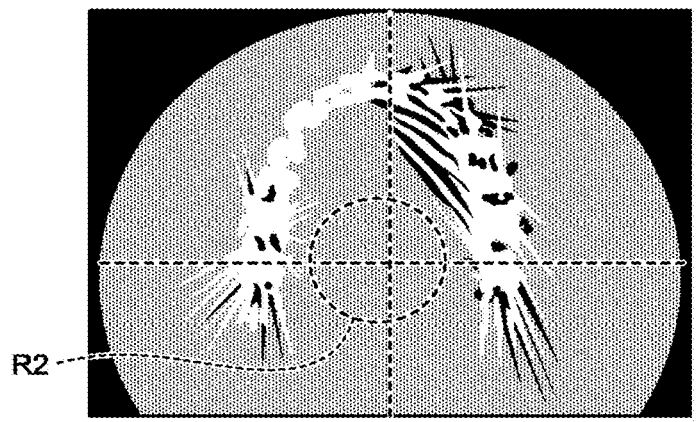
FIG. 12C is a drawing illustrating yet another example of the metal artifact reducing process performed by the X-ray CT apparatus according to the first embodiment.

With this arrangement, it is possible to generate a CT image in which no metal artifact occurs in the region of interest R2 designated by the operator. FIG. 12C is a drawing illustrating yet another example of the metal artifact reducing process performed by the X-ray CT apparatus 1 according to the first embodiment. FIG. 12C illustrates a CT image obtained by changing the X-ray paths so as to extend along the straight line L6 illustrated in the bottom section of FIG. 12B and performing a metal artifact reducing process. As illustrated in FIG. 12C, when the X-ray paths are changed so as to extend along the straight line L6, no metal artifact occurs in the region of interest R2. Accordingly, the viewer is able to evaluate the region of interest R2 in detail. This result was achieved because the group of metal pieces illustrated on the right side in FIG. 12B are not positioned on mutually the same set of paths, and the metal artifacts were therefore sufficiently reduced by the metal artifact reducing process.

When it is learned that a metal artifact inevitably occurs in the region of interest R2 no matter what set of paths is established, the deriving function 37*b* derives such a set of paths that makes the smallest impact, as the set of paths to be used in the main scan. For example, the deriving function 37*b* estimates the degree of metal artifacts occurring in the region of interest R2, for each candidate for the set of paths and further derives one of the candidates for a set of paths having the lowest estimated degree of metal artifacts as the set of paths to be used in the main scan. Further, when the degrees of metal artifacts are equal between two or more candidates for the set of paths, the deriving function 37*b* derives the two or more candidates for the set of paths, as sets of paths to be used in the main scan. In that situation, for example, the controlling function 37*d* may acquire projection data by using each of the two or more candidates for the set of paths that were derived. Further, the X-ray CT apparatus 1 may combined together two or more pieces of CT image data reconstructed from the pieces of projection data each of which is acquired by using a different one of the candidates for the set of paths. In other words, the X-ray CT apparatus 1 may extract a region including no metal artifact from each of the pieces of CT image data so as to generate combined data by combining together the extracted regions.

Further, the X-ray CT apparatus 1 is also capable of receiving an operation to designate a region such as a metal region and deriving such a set of paths that avoids the received region. For example, the input circuitry 31 receives an operation to designate a predetermined region of the subject. After that, the deriving function 37*b* derives a set of paths obtained by eliminating the predetermined region received by the input circuitry 31 from a previous set of X-ray paths. In this situation, the input circuitry 31 receives, as the predetermined region, one selected from among the following: a region indicating metal artifacts in the position determining image acquired from the subject; a region indicating a highly X-ray absorbent member within the position determining image; and a tooth region of the subject designated by a dental system.

Figure 13A:
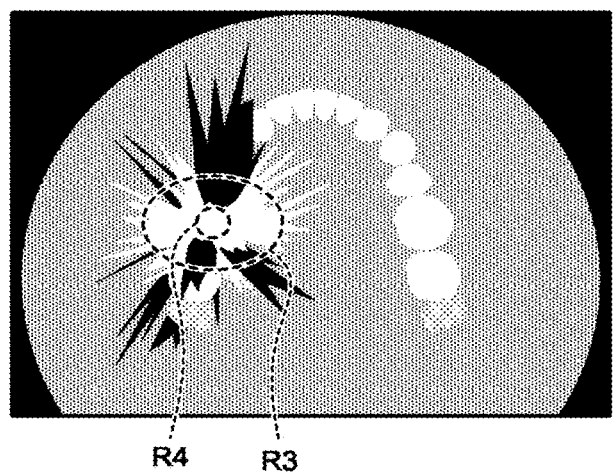
FIG. 13A is a drawing illustrating an example of a region setting process according to the first embodiment.

FIG. 13A is a drawing illustrating an example of a region setting process according to the first embodiment. FIG. 13A illustrates an axial cross-sectional image of the oral cavity generated from CT image data of a position determining image acquired three-dimensionally. For example, the operator refers to the axial cross-sectional image illustrated in FIG. 13A and designates a region such as the region R3 or the region R4. In other words, by referring to the position determining image and designating an unreliable region, the operator is able to determine a set of paths so that the designated region is not included in the set of paths. For example, when it is not possible to properly extract metal regions during the metal position information obtaining process performed by the obtaining function 37a, the operator may designate one or more regions such as the metal regions.

In this situation, the operator is able to designate any of various types of regions. For example, as indicated by the region R3 in FIG. 13A, the operator may designate a region including an artifact. In another example, as indicated by the region R4 in FIG. 13A, the operator may designate a region suspected to be a metal region. In this situation, the image referred to by the operator may arbitrarily be changed. In other words, it is acceptable to display an arbitrary cross-sectional image when the position determining image was acquired three-dimensionally.

For example, the operator designates the region including an artifact or the metal region, while changing the position of the cross-sectional plane for the cross-sectional image displayed on the display 32, by operating the input circuitry 31. As a result, the operator is able to input three-dimensional position information with respect to the region including the artifact or the metal region. The obtaining function 37a obtains the three-dimensional position information of the region R3 or the region R4 input via the input circuitry 31. After that, the deriving function 37b derives X-ray paths, on the basis of the three-dimensional position information of the region R3 or the region R4 obtained by the obtaining function 37a.

Further, the obtaining function 37a is also able to obtain the region R3 or the region R4 designated in the cross-sectional image as a region having a certain size that is set in advance. For example, the obtaining function 37a obtains a region prepared by stretching the designated region R3 or R4 in the front-and-back (depth) direction, as a three-dimensional region. In this situation, it is acceptable to arbitrarily set the amount by which the region is stretched. Alternatively, the obtaining function 37a may obtain a three-dimensional region by regarding the designated region as a sphere. With any of these arrangements, the operator is able to designate a three-dimensional region without the need to designate a region in each of the cross-sectional images obtained by changing the position.

Figure 13B:
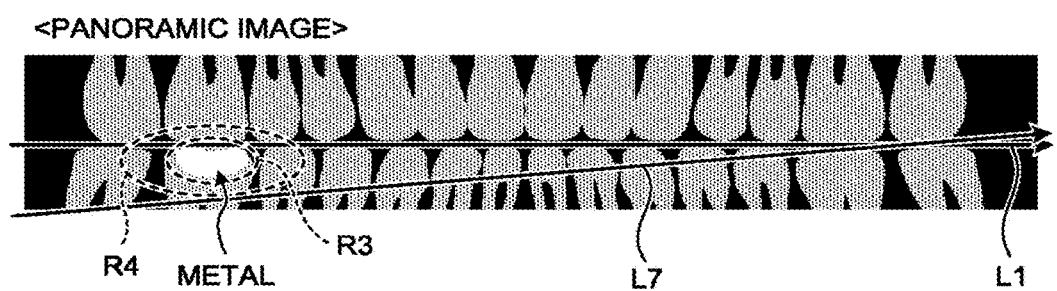
FIG. 13B is a drawing illustrating yet another example of the X-ray path deriving process performed by the deriving function according to the first embodiment.

When the obtaining function 37a has obtained the position information of the designated region in this manner, the deriving function 37b derives such a set of paths that does not include the designated three-dimensional region, on the basis of the obtained position information. FIG. 13B is a drawing illustrating yet another example of the X-ray path deriving process performed by the deriving function according to the first embodiment. For example, as illustrated in FIG. 13B, the deriving function 37b derives the straight line L7 avoiding the three-dimensional region R3 or R4 designated in the position determining image, as a set of X-ray paths to be used in the main scan. After that, for example, the controlling function 37d controls the gantry 10 and the couch device 20 so that the X-ray paths used in the main scan extend along the straight line L7. The straight line L7 in FIG. 13B illustrates the set of paths derived for the purpose of avoiding the region R4. In the situation where the designated region is only the region R3, a set of paths is established by changing the straight line L1 by a smaller angle.

In the description above, the example is explained in which the region is designated within the position determining image; however, when the imaged site is the oral cavity, it is also acceptable to designate one or more regions by using tooth numbers. For example, by looking at the inside of the oral cavity of the subject, the viewer is able to recognize the tooth numbers of the teeth on which metal pieces are placed. Accordingly, when the input circuitry 31 has received an operation to input the tooth numbers of the teeth on which the metal pieces are placed, the obtaining function 37a is able to obtain the position information of the metal pieces.

In this situation, the input circuitry 31 receives the designation of the tooth numbers described above, according to various dental systems including the Zsigmondy system (a Japanese system), the Universal System (the American Dental Association [ADA] system; an American system), and the Two-Digit System (the Fédération Dentaire Internationale [FDI] system). The Zsigmondy system may also be called the Zsigmondy's system. Further, the ADA system may also be called the Universal Numbering System or an American system. Further, the FDI system may also be called the Two-Digit Numbering System, the ISO system, or the FDI system. When an imaged row of teeth has a (congenital or acquired) missing tooth or a supernumerary tooth, or when a row of teeth is imaged during a mixed dentition period in which deciduous teeth are replaced by permanent teeth, it is possible to convert the tooth numbers of the corresponding site into an arbitrary symbols/numbers no matter which dental system is being used. FIG. 14 is a drawing illustrating examples of the dental systems received by the input circuitry 31 according to the first embodiment. FIG. 14 indicates the numbers of permanent teeth without parentheses and the numbers of deciduous teeth in parentheses. The drawing in FIG. 14 illustrates rows of permanent teeth. (No rows of deciduous teeth are illustrated.) For example, when the X-ray CT apparatus 1 is used in Japan, the input circuitry 31 receives an operation to designate tooth numbers according to the dental system called the Zsigmondy system (the Japanese system) illustrated in FIG. 14. In other words, as illustrated in FIG. 14, the input circuitry 31 receives the tooth numbers according to the dental system in which the rows of teeth are divided into the four sections of "upper right" "upper left", "lower right", and "lower left", so that the permanent teeth are numbered "1 to 8" and the deciduous teeth are identified as "A to E (or I to V)", from the center (the front) to the distal ends (the rear) in each of the sectional regions.

In another example, when the X-ray CT apparatus 1 is internationally used in Europe or the like, the input circuitry 31 receives an operation to designate tooth numbers according to the dental system called the Two-Digit System (the FDI system) illustrated in FIG. 14. In other words, as illustrated in FIG. 14, the input circuitry 31 receives the tooth numbers according to the dental system in which the rows of teeth are divided into four sections so that the permanent teeth are numbered "11 to 18" and the deciduous teeth are numbered "51 to 55" from the front to the rear in the upper right region; the permanent teeth are numbered "21 to 28" and the deciduous teeth are numbered "61 to 65" from the front to the rear in the upper left region; the permanent teeth are numbered "31 to 38" and the deciduous teeth are numbered "71 to 75" from the front to the rear in the lower left region; and the permanent teeth are numbered "41 to 48" and the deciduous teeth are numbered "81 to 85" from the front to the rear in the lower right region.

In yet another example, when the X-ray CT apparatus 1 is used in the USA or the like, the input circuitry 31 receives an operation to designate tooth numbers according to the dental system called the Universal System (the ADA system; the American system) illustrated in FIG. 14. In other words, as illustrated in FIG. 14, the input circuitry 31 receives the tooth numbers according to the dental system in which the permanent teeth are numbered "1 to 16" and the deciduous teeth are numbered "D1 to D10" from the right rear to the left rear of the row of teeth on the upper jaw; and the permanent teeth are numbered "17 to 32" and the deciduous teeth are numbered "D11 to D20" from the left rear to the right rear of the row of teeth on the lower jaw.

For example, the input circuitry 31 receives an operation to designate the tooth numbers of the teeth on which the metal pieces are placed, by using one of the dental systems explained above. The deriving function 37b extracts tooth regions included in a position determining image and further derives a set of paths so that such tooth regions that are among the extracted tooth regions and that correspond to the designated tooth numbers are not included in the set of paths. After that, the controlling function 37d controls the gantry 10 and the couch device 20 so that the X-ray paths to be used in the main scan are the derived set of paths.

In this situation, before acquiring the position determining image, the input circuitry 31 is able to receive the operation to designate the tooth numbers according to any of the dental systems. In that situation, for example, the deriving function 37b is also capable of deriving approximate information of the paths on the basis of a typical dental structure. In other words, on the assumption that rows of teeth having the typical structure are arranged with the gantry 10, the deriving function 37b derives information about an optimal set of paths corresponding to when metal pieces are placed on the teeth identified by the designated numbers. For example, when a plurality of tooth numbers are designated by using one of the dental systems, the deriving function 37b derives a set of X-ray paths, so that among the plurality of tooth regions corresponding to the designated tooth numbers, the quantity of tooth regions positioned on mutually the same set of paths is one or smaller. The deriving function 37b is also capable of deriving a set of X-ray paths in this manner in advance and making corrections for each subject after a position determining image is acquired.

The input circuitry 31 is also able to receive an operation to designate information about a mode of the metal pieces placed on the teeth. For example, it is possible to improve the level of precision in the path information deriving process performed by the deriving function 37b, by configuring the input circuitry 31 to receive information about any of the following: a mode in which a metal piece such as an inlay or an amalgam piece is locally placed in a part of the crown of a tooth; a mode in which a metal piece such as an artificial crown is placed so as to replace the crown of a tooth; a mode in which a metal piece such as a metal core is placed so as to further fill the pulp cavity; and a combination of any of these modes.

The X-ray path deriving processes and the control exercised to acquire the CT image data by using the derived paths have thus been explained. The X-ray CT apparatus 1 according to the first embodiment is also capable of causing the display 32 to display the information about the derived X-ray paths. More specifically, as the information about the X-ray paths, the display controlling function 37c causes the display 32 to display at least one selected from among the following: a position determining image indicating the X-ray paths; image information indicating a posture of the subject used for setting X-ray paths in accordance with the processing effect of the metal artifact reducing process performed on the highly X-ray absorbent members; and a simulation image corresponding to when an acquiring process is performed by setting X-ray paths in accordance with the processing effect of the metal artifact reducing process performed on the highly X-ray absorbent members.

Figure 15:
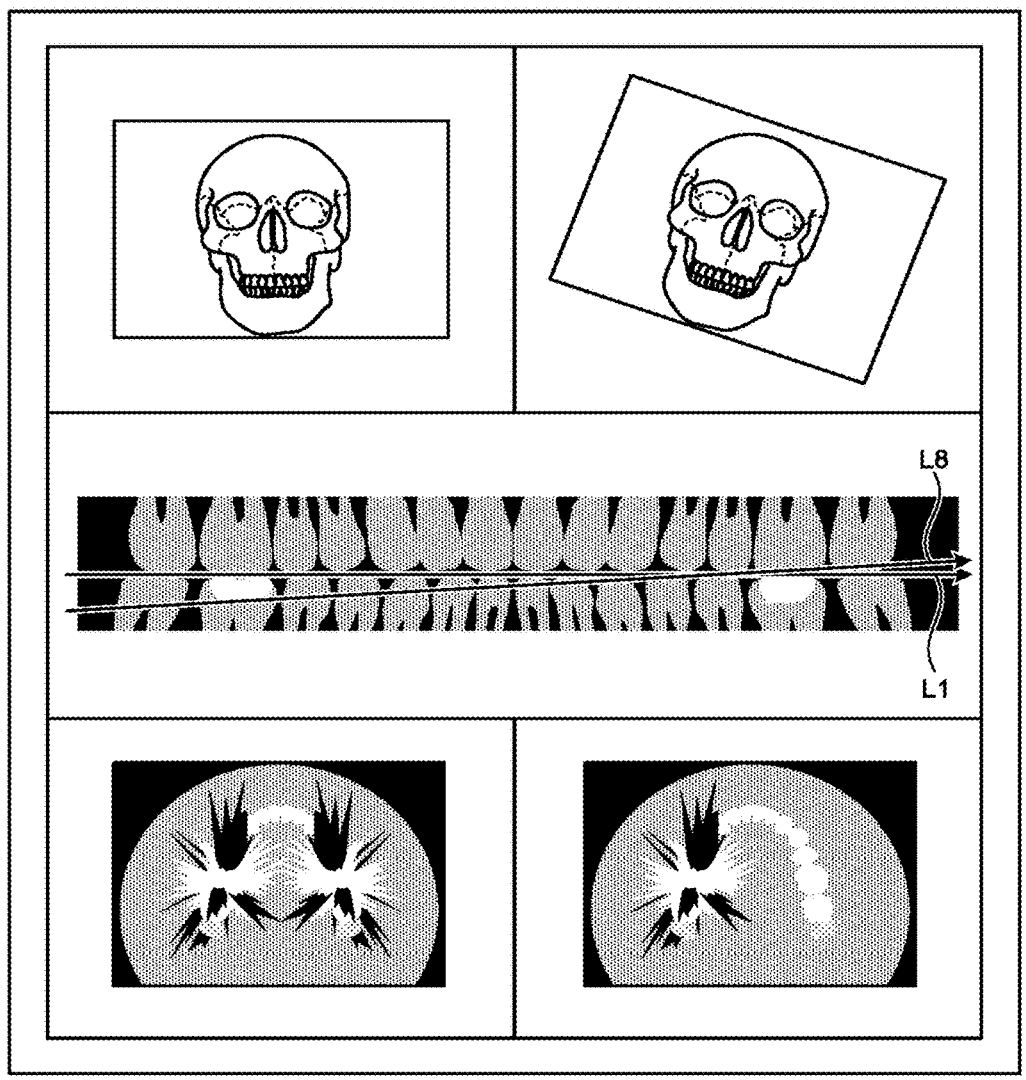
FIG. 15 is a drawing illustrating an example of a display realized by a display controlling function according to the first embodiment.

FIG. 15 is a drawing illustrating an example of a display realized by a display controlling function 37c according to the first embodiment. FIG. 15 illustrates a planning screen for a main scan. For example, as illustrated in the top section of FIG. 15, the display controlling function 37c displays, on the planning screen, CT images indicating postures of the subject used for setting X-ray paths. In other words, the display controlling function 37c displays, on the planning screen, a CT image indicating the state of the subject before changing the paths as indicated in the upper left section of FIG. 15 and a CT image indicating the state of the subject after changing the paths as indicated in the upper right section of FIG. 15.

In this situation, the CT image illustrated in the upper section of FIG. 15 indicates the state of the subject with respect to the X-Y plane of the gantry 10. In other words, the operator is able to recognize at a glance that it is possible to change the X-ray paths into a set of paths that is suitable for the metal artifact reducing process, by tilting the subject to the right with respect to the X-Y plane. Further, as illustrated in the middle section of FIG. 15, the display controlling function 37c displays, on the planning screen, a display image obtained by superimposing the straight line L1 indicating the set of paths before the change and a straight line L8 indicating a set of paths after the change, on a panoramic image. Further, as illustrated in the bottom section of FIG. 15, the display controlling function 37c displays a simulation image corresponding to when the paths have been changed. For example, as illustrated in the lower right section of FIG. 15, the display controlling function 37c displays the simulation image corresponding to when the paths have been changed so as to be arranged next to the image from before the change. In this situation, the images illustrated in FIG. 15 are generated by the image reconstructing circuitry 36, by using already-acquired image data (e.g., data of a position determining image or data of a simple image).

In this situation, the images illustrated in FIG. 15 function as a GUI and are also displayed in conjunction with one another. In other words, the display controlling function 37c displays the images after changing the state thereof, in accordance with an operation to change any of the images illustrated in FIG. 15. In one example, via the input circuitry 31, the operator is able to perform an operation to change the angle of the image indicating the state of the subject and being displayed on the planning screen. In that situation, the display controlling function 37c displays the straight line L8 in the panoramic image by changing the slope thereof in an amount equal to the angle changed by the operator. Further, the display controlling function 37c displays a simulation image for a set of paths corresponding to the angle changed by the operator. The input circuitry 31 is also capable of receiving an operation to change the angle of the straight line L8 in the panoramic image. In that situation, the display controlling function 37c displays, on the planning screen, an image in which the state of the subject has been changed in accordance with the change made to the angle of the straight line L8 as well as a simulation image.

In the embodiment described above, the example is explained in which the three-dimensional position determining image is acquired, so that the X-ray paths are derived on the basis of the position information of the metal pieces included in the acquired position determining image. However, possible embodiments are not limited to this example. For instance, it is also acceptable to acquire a two-dimensional position determining image. In that situation, the obtaining function 37a obtains the position information of the metal pieces from the two-dimensional position determining image. After that, the deriving function 37b derives X-ray paths on the basis of the obtained position information.

Figure 16:
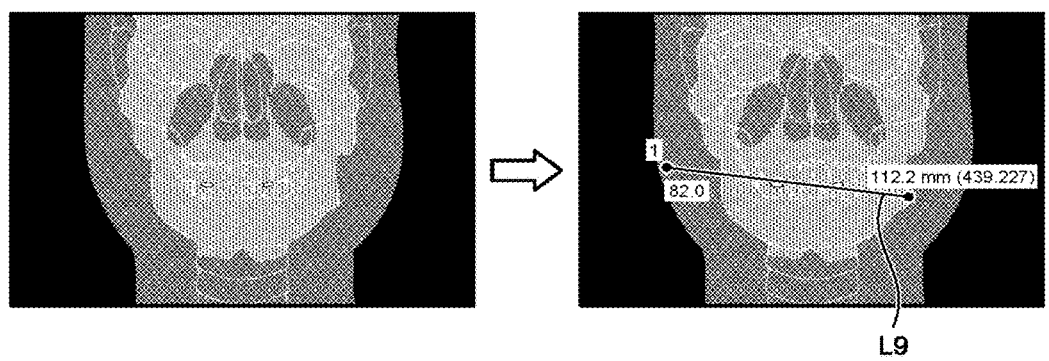
FIG. 16 is a drawing illustrating yet another example of the X-ray path deriving process performed by the deriving function according to the first embodiment.

FIG. 16 is a drawing illustrating yet another example of the X-ray path deriving process performed by the deriving function 37b according to the first embodiment. FIG. 16 illustrates position determining images acquired two dimensionally. For example, on the basis of degrees of X-ray absorption, the obtaining function 37a extracts metal regions from the position determining image illustrated in FIG. 16. Subsequently, as illustrated in FIG. 16, the deriving function 37b derives a straight line L9 so that the extracted metal regions are not included in mutually the same set of paths, as a set of paths to be used in the main scan.

Next, a process performed by the X-ray CT apparatus 1 according to the first embodiment will be explained, with reference to FIG. 17. FIG. 17 is a flowchart illustrating a procedure in the process performed by the X-ray CT apparatus 1 according to the first embodiment. Step S101 in FIG. 17 is a step executed as a result of the processing circuitry 37 reading the program corresponding to the controlling function 37d from the storage circuitry 35. At step S101, the processing circuitry 37 acquires a position determining image (a scanogram image) by controlling the scan controlling circuitry 33, the image reconstructing circuitry 36, and the like.

Step S102 in FIG. 17 is a step executed as a result of the processing circuitry 37 reading the program corresponding to the obtaining function 37a from the storage circuitry 35. At step S102, the processing circuitry 37 obtains position information of metal pieces in the position determining image. Step S103 is a step executed as a result of the processing circuitry 37 reading the program corresponding to the deriving function 37b from the storage circuitry 35. At step S103, the processing circuitry 37 derives X-ray paths in accordance with the processing effect of a metal artifact reducing process, on the basis of the position information of the metal pieces.

Step S104 is a step executed as a result of the processing circuitry 37 reading the program corresponding to the controlling function 37d from the storage circuitry 35. At step S104, the processing circuitry 37 calculates an acquisition condition used for performing a main scan by using the X-ray paths. Steps S105 through S107 are steps executed as a result of the processing circuitry 37 reading the program corresponding to the controlling function 37d from the storage circuitry 35. At step S105, the processing circuitry 37 judges whether or not a simulation is to be performed by using the derived X-ray paths. When the processing circuitry 37 determines that no simulation is to be performed (step S105: No), the process proceeds to step S106. On the contrary, when the processing circuitry 37 determines that a simulation is to be performed (step S105: Yes), the process proceeds to step S107. The judgement as to whether a simulation is to be performed or not is made depending on whether the quantity of metal regions obtained by the obtaining function 37a exceeds a predetermined value or whether the positional relationship among the plurality of metal pieces is a predetermined positional relationship. In other words, the controlling function 37d judges whether or not the simulation is to be performed on the basis of the judgment conditions described above.

At step S106, the processing circuitry 37 causes the calculated acquisition condition to be presented. For example, by controlling the light projector 17, the processing circuitry 37 arranges angle information indicating the calculated acquisition condition to be presented with a laser beam of the light projector 17. At step S107, the processing circuitry 37 performs a simulation by using the derived X-ray paths. Step S108 is a step executed as a result of the processing circuitry 37 reading the program corresponding to the display controlling function 37c from the storage circuitry 35. At step S108, the processing circuitry 37 causes the display 32 to display a result of the simulation of the situation where the main scan is performed by using the derived paths.

Steps S109 through S112 are steps executed as a result of the processing circuitry 37 reading the program corresponding to the controlling function 37d from the storage circuitry 35. At step S109, the processing circuitry 37 judges whether or not an operation to control the gantry 10 and the couch device 20 has been received. When the operation has been received (step S109: Yes), the processing circuitry 37 controls the gantry 10 and the couch device 20 at step S110. At step S111, it is judged whether or not an operation to start a scan has been received. When it is determined in the judging process at step S109 that the operation has not been received (step S109: No), the processing circuitry 37 proceeds to step S111.

When it is determined in the judging process at step S111 that an operation to start a scan has been received (step S111: Yes), the processing circuitry 37 starts the main scan at step S112. In this situation, the processing circuitry 37 has been in a standby state until the operation to start the scan is received (step S111: No).

As explained above, according to the first embodiment, the data acquiring circuitry 14 is configured to detect the X-rays that have passed through the subject by using the detector and to acquire the projection data on the basis of the detection result. The obtaining function 37a is configured to obtain the position information of the metal pieces in the body of the subject. The deriving function 37b is configured to derive the information about the X-ray paths in accordance with the processing effect of the metal artifact reducing process performed on the metal pieces, on the basis of the position information of the metal pieces. Accordingly, the X-ray CT apparatus 1 according to the first embodiment is capable of deriving the X-ray paths in accordance with the processing effect of the metal artifact reducing process. Further, by performing the main scan by using the derived paths, the X-ray CT apparatus 1 makes it possible to further reduce the metal artifacts.

Further, according to the first embodiment, the deriving function 37b is configured to derive the information about the X-ray paths, so as to reduce the metal artifacts in the region of interest within the image data reconstructed from the projection data, during the metal artifact reducing process. Accordingly, the X-ray CT apparatus 1 according to the first embodiment is able to reduce the metal artifacts in the region which the user wishes to evaluate and thus makes it possible to improve the level of precision of diagnosing processes.

Further, according to the first embodiment, the deriving function 37b is configured to derive the information about the X-ray paths that keep the quantity of metal pieces positioned on the X-ray paths one or smaller. Accordingly, even when the metal pieces are included in the paths, the X-ray CT apparatus 1 according to the first embodiment makes it possible to effectively eliminate the artifacts by performing the metal artifact reducing process.

Further, according to the first embodiment, the deriving function 37b is configured to derive the information about the X-ray paths that minimize the quantity of metal pieces positioned on the X-ray paths. Accordingly, even when metal pieces in a large quantity are included, the X-ray CT apparatus 1 according to the first embodiment is capable of deriving such paths that maximize the effect of the metal artifact reducing process.

Further, according to the first embodiment, the deriving function 37b is configured to derive the information about the X-ray paths obtained by eliminating, from the previous X-ray paths, at least the most highly X-ray absorbent metal piece among the plurality of metal pieces placed in the body of the subject. Accordingly, the X-ray CT apparatus 1 according to the first embodiment makes it possible to selectively eliminate the metal piece that is most likely to cause an artifact, from the paths.

Further, according to the first embodiment, the input circuitry 31 is configured to receive the operation of designating the predetermined region of the subject. The deriving function 37b is configured to derive the information about the X-ray paths obtained by eliminating, from the previous X-ray paths, the predetermined region received by the input circuitry 31. Further, the input circuitry 31 receives, as the predetermined region, one selected from among the following: the region indicating the metal artifacts within the position determining image acquired from the subject; the region indicating the metal piece within the position determining image; and the tooth region of the subject designated by using any one of the dental systems. Accordingly, the X-ray CT apparatus 1 according to the first embodiment makes it possible to derive the X-ray paths eliminating the region desired by the operator.

Further, according to the first embodiment, the dental systems include the Zsigmondy system (the Japanese system), the ADA system (the American system), and the FDI system. Accordingly, the X-ray CT apparatus 1 according to the first embodiment makes it possible to designate the tooth numbers by using any of the various dental systems.

Further, according to the first embodiment, the controlling function 37d is configured to set the acquisition condition for acquiring the projection data, on the basis of the information about the X-ray paths. The data acquiring circuitry 14 is configured to acquire the projection data by using the set acquisition condition. Further, the acquisition condition is at least one selected from among the following: the tilt angle of the gantry 10 including the X-ray source; the rotation angle of the gantry 10; and the rotation angle of the couch device 20 on which the subject is lying. Accordingly, the X-ray CT apparatus 1 according to the first embodiment makes it possible to acquire the projection data after changing the X-ray paths without imposing a burden on the subject.

Further, according to the first embodiment, the controlling function 37d is configured to control the light projector 17 so as to project the light to the position on the body surface of the subject corresponding to the information about the X-ray paths. Further, as the information about the X-ray paths, the display controlling function 37c is configured to cause the display 32 to display at least one selected from among the following: the position determining image indicating the X-ray paths; the image information indicating the posture of the subject used for setting the X-ray paths in accordance with the processing effect of the metal artifact reducing process performed on the metal pieces; and the simulation image corresponding to when an acquiring process is performed by setting the X-ray paths in accordance with the processing effect of the metal artifact reducing process performed on the metal pieces. Accordingly, the X-ray CT apparatus 1 according to the first embodiment makes it possible to visually recognize how the X-ray paths are changed.

Further, according to the first embodiment, the obtaining function 37a is configured to obtain the position information of the metal pieces in the body of the subject, on the basis of the CT values of the position determining image of the subject. Accordingly, the X-ray CT apparatus 1 according to the first embodiment makes it possible to easily obtain the position information of the metal pieces.

Second Embodiment

In the first embodiment described above, the example is explained in which the X-ray paths are changed as a result of the controlling function 37d controlling the gantry 10 and the couch device 20. In a second embodiment, an example will be explained in which the X-ray paths are changed by changing the state of the subject. More specifically, the X-ray CT apparatus 1 according to the second embodiment has an aiding tool configured to change the posture of the subject, for the purpose of setting X-ray paths in accordance with the processing effect of the metal artifact reducing process performed on the metal pieces.

Figure 18A:
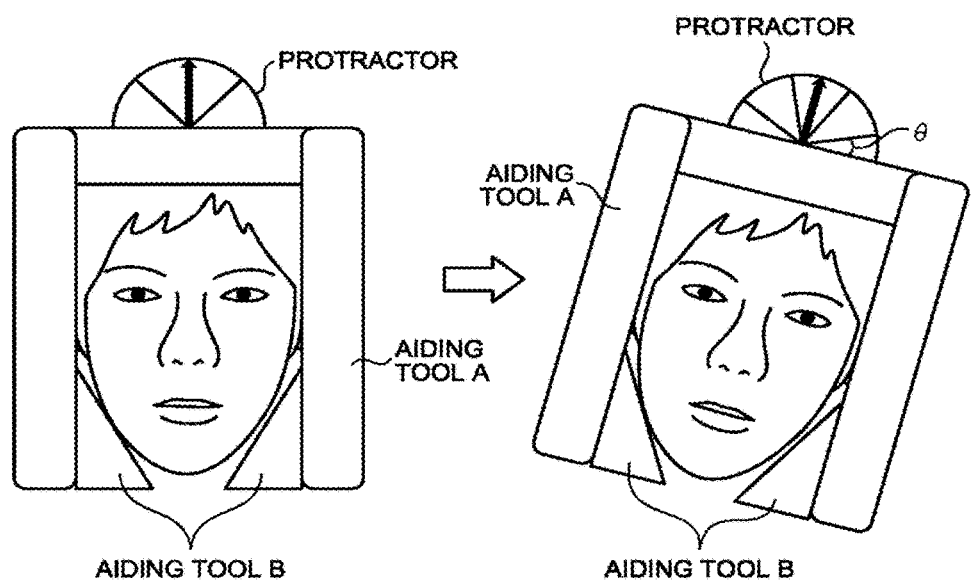
FIG. 18A is a drawing illustrating an example of an aiding tool according to a second embodiment.
Figure 18B:
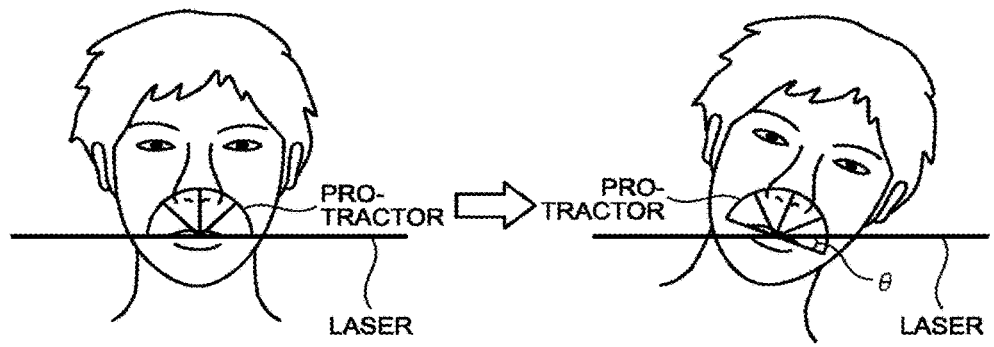
FIG. 18B is a drawing illustrating another example of the aiding tool according to the second embodiment.

FIGS. 18A and 18B are drawings illustrating examples of aiding tools according to the second embodiment. For example, the aiding tools include, as illustrated in FIG. 18A, an aiding tool A attached to the head of the subject and an aiding tool B configured to prevent the subject from moving within the aiding tool A. Further, as illustrated in FIG. 18A, the aiding tools include a protractor. For example, the protractor provided for the aiding tool is configured to be able to measure the tilting of the head. As illustrated in FIG. 18A, the protractor is able to display the angle "θ" corresponding to the tilting of the head of the subject. In other words, when the posture of the subject is to be changed by an amount corresponding to the angle of the set of X-ray paths derived by the deriving function 37b, the operator is able to change the posture of the subject on the basis of the angle indicated by the protractor. In one example, when the set of paths indicated by the straight line L1 in FIG. 4 is tilted by "5 degrees" so as to be changed into the set of paths indicated by the straight line L2, the operator tilts the face of the subject so that the angle "θ" indicated by the protractor illustrated in FIG. 18A is equal to "5 degrees".

Further, as illustrated in FIG. 18B, it is also acceptable to use only the protractor as an aiding tool. For example, as illustrated in FIG. 18B, it is possible to change the posture of the subject by an amount corresponding to the angle of the X-ray paths derived by the deriving function 37b, by prompting the subject to hold the protractor in his/her mouth and to tilt his/her face to achieve an alignment with the laser beam emitted from the light projector 17. In one example, as illustrated in FIG. 18B, it is possible to measure the angle by which the subject's face is tilted, by using the angle "θ" indicated by the laser beam on the protractor held in the mouth of the subject. Further, possible embodiments of the aiding tools are not limited to those illustrated in FIG. 18A. It is acceptable to use any of other various types of aiding tools. For example, it is also acceptable to use an aiding tool including a gyro sensor or the like.

Further, for example, the aiding tool does not necessarily have to be configured to calculate the angle as described above. The aiding tool may be worn so that the imaged site is positioned at an angle set in advance. In one example, when the imaged site is the oral cavity, it is acceptable to use a mouthpiece configured to shift the teeth on the upper jaw and the teeth on the lower jaw at a predetermined angle with respect to each other. For example, it is acceptable to prepare a plurality of mouthpieces in advance for shifting the teeth on the upper jaw and the teeth on the lower jaw at various angles with respect to each other, so that an optimal one of the mouthpieces is selected in accordance with the paths derived by the deriving function 37b. In that situation, to perform an image taking process on the head of the subject, when metal pieces are placed in a teeth part of the subject, the selecting function 37e is configured to select one of the mouthpieces used for eliminating one or more of the metal pieces from the X-ray paths, on the basis of the information about the X-ray paths. With this arrangement, it is possible to easily position the site at the angle.

As explained above, according to the second embodiment, the aiding tools are configured to change the posture of the subject, for the purpose of setting the X-ray paths in accordance with the processing effect of the metal artifact reducing process performed on the metal pieces. Accordingly, the X-ray CT apparatus 1 according to the second embodiment is able to easily set the X-ray paths derived by the deriving function 37b, only by changing the posture of the subject.

Third Embodiment

In a third embodiment, an example will be explained in which a main scan is performed by using the paths that were set. For example, the X-ray CT apparatus 1 according to the third embodiment is configured to display, together with a CT image of the main scan, display information indicating the condition under which the main scan was performed. More specifically, the display controlling function 37c causes the display 32 to display the CT image based on projection data acquired on the basis of the information about the X-ray paths derived by the deriving function 37b and the acquisition condition of the projection data.

Figure 19:
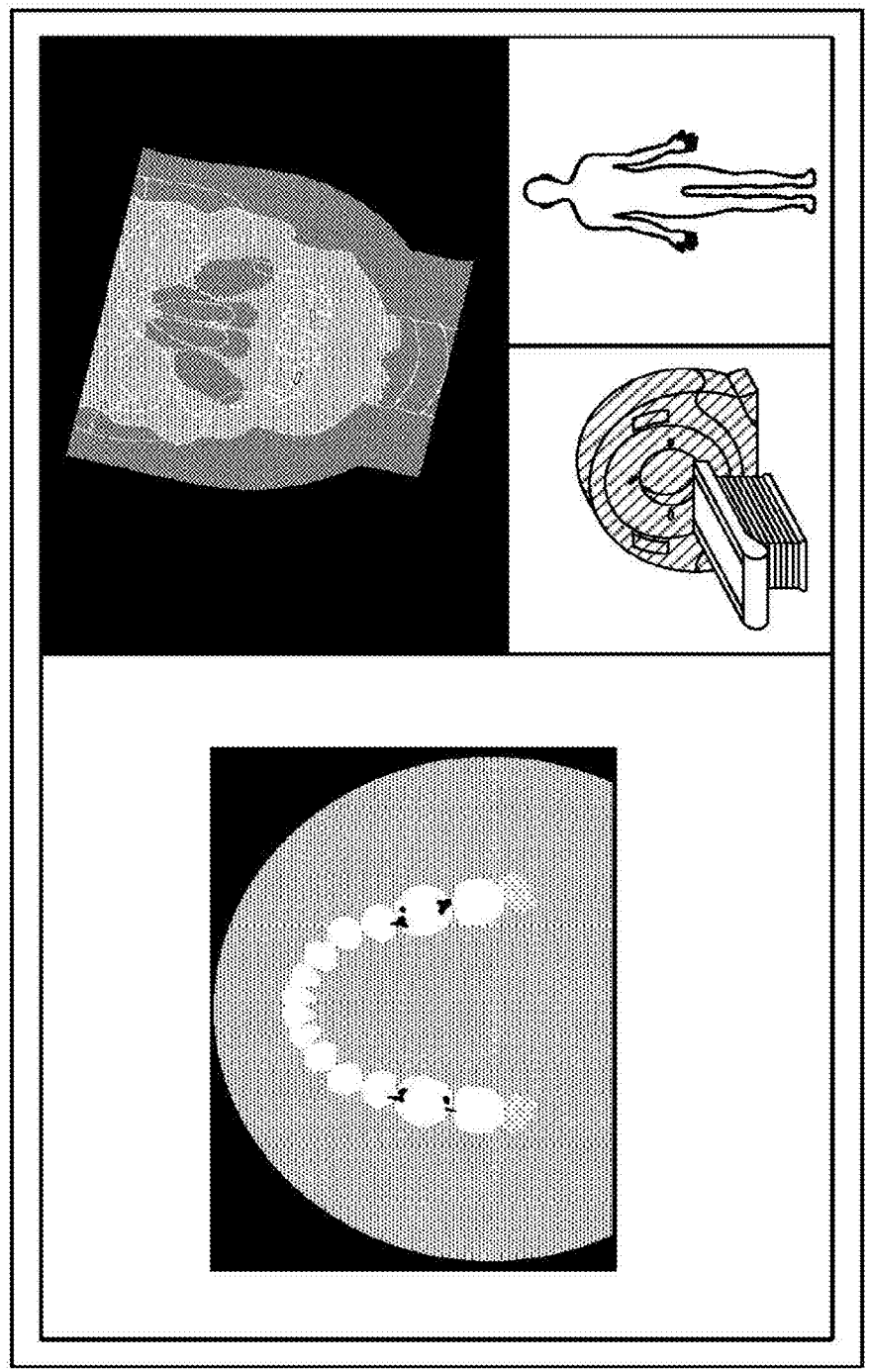
FIG. 19 is a drawing illustrating an example of a display realized by a display controlling function according to a third embodiment.

FIG. 19 is a drawing illustrating an example of a display realized by the display controlling function 37c according to the third embodiment. For example, as illustrated in FIG. 19, the display controlling function 37c causes the display 32 to display, in addition to a CT image (in the left section of the drawing) of the inside of the oral cavity acquired by performing the main scan, another CT image (in the upper right section of the drawing) indicating the state of the subject during the main scan, as well as information (in the lower right section of the drawing) indicating the changed conditions. In this situation, the display controlling function 37c arranges the CT image of the inside of the oral cavity used for an image interpretation process, to be displayed as an image suitable for the image interpretation process. More specifically, because the main scan was performed with a tilt of a predetermined angle, the sites rendered in the acquired CT image data are also tilted with respect to the X-Y-Z axes. For this reason, the display controlling function 37c controls the image reconstructing circuitry 36 to generate a CT image on an axial cross-sectional plane orthogonal to the body-axis direction and causes the display 32 to display the generated CT image. As a result, the X-ray CT apparatus 1 is able to arrange the CT image suitable for the image interpretation process to be displayed automatically.

Further, the display controlling function 37c is configured to cause a CT image indicating the state of the subject during the main scan to be displayed separately from the CT image suitable for the image interpretation process. With this arrangement, the X-ray CT apparatus 1 is able to help the viewer to understand a cause of deformation of a soft tissue or the like. For example, as illustrated in FIG. 19, when the face of the subject is tilted, the state of a soft tissue in the neck of the subject or the like is different from the state observed when the face is straight. When viewing only the CT image for the image interpretation purpose, it is difficult for an image reading doctor to understand the cause of the change in the state. However, when the CT image indicating the state of the subject during the main scan is displayed next to the other CT image, the image reading doctor is able to easily understand the cause.

Further, the display controlling function 37c is configured to further display information indicating whether the change in the state of the subject during the main scan is caused by the control exercised on the gantry 10 and the couch device 20 or the change is caused due to a change in the posture of the subject himself/herself. For example, as illustrated in FIG. 19, by changing the color of the information representing the gantry 10, the display controlling function 37c realizes a display indicating that the change in the state of the subject is caused by the control exercised on the slewing mechanism or the tilting mechanism of the gantry 10. In another example, when the state of the subject is changed due to the slewing mechanism of the couch device 20, the display controlling function 37c realizes a display by changing the color of the information representing the couch device 20. Further, when the posture of the subject himself/herself is changed, the display controlling function 37c realizes a display by changing the color of the information representing the subject.

FIG. 19 illustrates the example in which the cause of the change in the state of the subject during the main scan is indicated by realizing the display in which the information representing the gantry 10, the information representing the couch device 20, or the information representing the subject is colored. However, possible embodiments are not limited to this example. For instance, it is also acceptable to further display the direction in which the change was made, or the like. For example, when the gantry 10 is tilted by the tilting mechanism, the display controlling function 37c may display the direction and/or the angle of the tilt. Similarly, when the gantry 10 has been rotated by the slewing mechanism, the display controlling function 37c may display the direction and/or the angle of the rotation. Further, when the couch device 20 has been rotated by the slewing mechanism, the display controlling function 37c may display the direction and/or the angle of the rotation. Further, when the posture of the subject himself/herself is changed, the display controlling function 37c may display information indicating the posture of the subject.

As explained above, according to the third embodiment, the display controlling function 37c is configured to cause the display 32 to display the CT image based on the projection data acquired on the basis of the information about the X-ray paths derived by the deriving function 37b, together with the acquisition condition of the projection data. Consequently, the X-ray CT apparatus 1 according to the third embodiment is able to help the viewer to understand the state of the subject during the main scan at a glance. The X-ray CT apparatus 1 therefore makes it possible to prevent the level of precision in the image interpretation process from being degraded.

Fourth Embodiment

The first to the third embodiments have thus been explained. The present disclosure may be carried out in other various forms besides those described in the first to the third embodiments.

In the embodiments described above, the examples are explained in which the present disclosure is applied to the intraoral metal. However, possible embodiments are not limited to those examples. It is possible to apply the present disclosure to any other various types of intracorporeal metal. For example, the present disclosure may be applied to stents or coils in blood vessels, screws or plates in bones and soft tissues, medical staples, and the like. For example, it is possible to apply the present disclosure to the following types of metal: For instance, in the "dental department", examples include dental implants in jaw bones, in addition to the intraoral metal pieces. Examples in the "surgical department" (which may also be covered in the dental department)" include medical staples, metal fixtures used for securing bones (e.g., plates, screws, wires, and the like), sternal wires, medical clips (cerebral artery clips, bile duct clips, and the like), implants (for eyeballs and the like), artificial joints, artificial bone heads, and the like. In the "cardiology department", examples include intravascular stents, metal coils, cardiac pacemakers, artificial valves, Inferior Vena Cava (IVC) filters, and the like. As for "unwanted metallic intracorporeal matters", examples include bullets and shotgun bullets remaining in the body, metal pieces remaining in the body, and the like. Further, in "other categories", examples include intrauterine devices.

Figure 20:
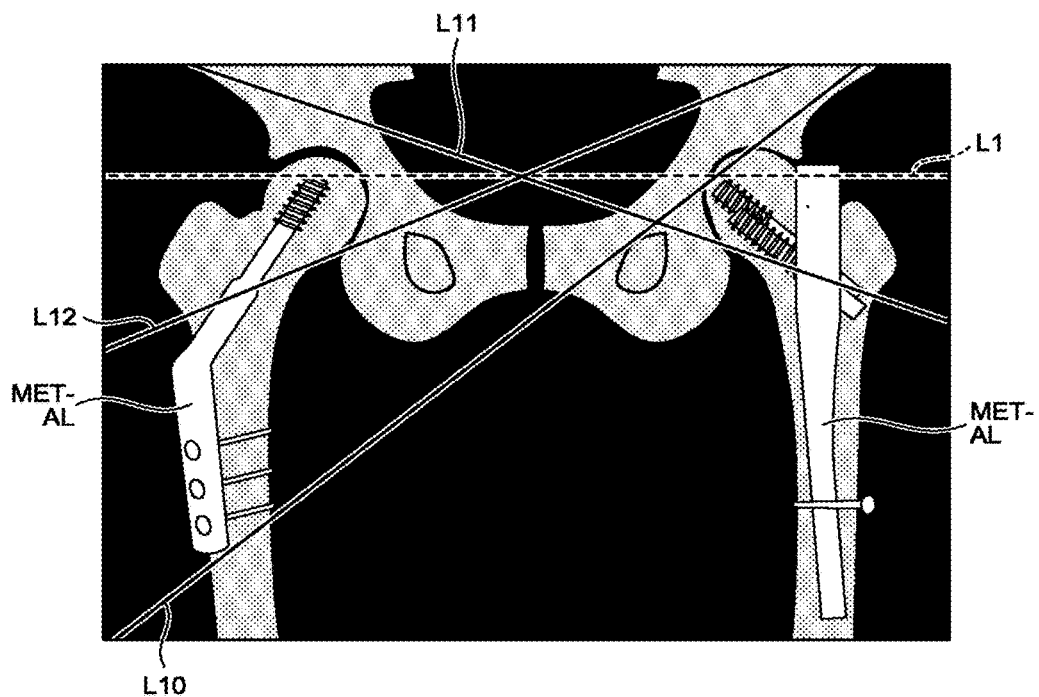
FIG. 20 is a drawing illustrating an example of an X-ray path deriving process performed by a deriving function according to the fourth embodiment.

Next, examples will be explained with reference to FIG. 20 in which the present disclosure is applied to metal pieces different from the intraoral metal pieces described above. FIG. 20 is a drawing illustrating another example of the X-ray path deriving process performed by the deriving function 37b according to a fourth embodiment. FIG. 20 illustrates an example in which an artificial bone head is placed in each of the two thighs. For example, as illustrated in FIG. 20, when the metal piece is placed in each of the two thighs, and a set of X-ray paths is set as indicated by the straight line L1, the two metal pieces are included in the straight line L1. When CT image data is acquired in this manner, the processing result of the metal artifact reducing process would be lowered.

To cope with this situation, the deriving function 37b derives a set of X-ray paths, on the basis of the position information of the metal pieces placed in the two thighs. For example, as a set of X-ray paths to be used in a main scan performed on the subject illustrated in FIG. 20, the deriving function 37b derives a straight line L10 illustrated in FIG. 20. In other words, as the set of X-ray paths, the deriving function 37b derives the straight line L10 so that neither of the metal pieces is included in the set of paths. In this situation, the deriving function 37b judges whether or not it is possible to realize the set of paths extending along the derived straight line L10. In other words, the deriving function 37b judges whether or not the derived straight line L10 is realizable in the control range of the gantry 10 and the couch device 20. When the derived straight line L10 is realizable, the deriving function 37b presents an acquisition condition used for performing an image taking process by using the derived straight line L10.

On the contrary, when the derived straight line L10 is not realizable, the deriving function 37b derives a realizable range within the control range of the gantry 10 and the couch device 20. For example, the deriving function 37b obtains information about a slewable movable range within the control range of the gantry 10 and the couch device 20 and further derives a movable range indicated by the straight lines L11 and L12 as illustrated in FIG. 20. In other words, as illustrated in FIG. 20, the deriving function 37b derives a range of paths in which it is possible to set the X-ray paths to be used in the main scan.

The display controlling function 37c presents the operator with the X-ray paths and the range of paths derived by the deriving function 37b. In this situation, on the thighs illustrated in FIG. 20 or the like, it is not possible to perform the image taking process by using pan tomography, unlike the examples of the teeth described above. Accordingly, for the purpose of setting the paths while taking the metal in the depth direction into consideration, a CT image generated by implementing a Ray Sum method (a sum projection method) or a CT image generated by implementing a Maximum Intensity Projection (MIP) method are used for the path setting process. For example, the display controlling function 37c presents the X-ray paths and the range of paths that were derived so as to be displayed in a Ray Sum image generated by implementing the Ray Sum method or in an MIP image generated by implementing the MIP method. The operator subsequently establishes a set of paths in the Ray Sum image or the MIP image being presented.

In the embodiments described above, the example is explained in which the main scan is performed on the inside of the oral cavity; however, the main scan does not necessarily have to be performed on the inside of the oral cavity and may be performed on any site selected from the whole body of the subject. In that situation, when the angle is changed with respect to the scan performed on the region in which a metal piece is placed, data may be missing between pieces of CT image data acquired during the main scan. In one example, when the angle of a set of X-ray paths for a region containing no metal piece is different from the angle of a set of X-ray paths for a region containing a metal piece, the CT image data may be missing in a section where the angle was changed. The X-ray CT apparatus 1 according to the fourth embodiment is able to set a scan range while making an adjustment thereto on a planning screen for the main scan.

FIG. 21 is a drawing for explaining a scan range setting process according to the fourth embodiment. With reference to FIG. 21, an example will be explained in which a scan is performed on the chest and the abdomen of a subject who has a metal piece in the chest. FIG. 21 illustrates the example in which a main scan is performed by using a W-Volume scan (for example, data is repeatedly acquired from a range that is 16 cm long in the body-axis direction, while sliding the subject along the body-axis direction). In that situation, the X-ray CT apparatus 1 according to the fourth embodiment derives a set of paths that optimizes the metal artifact reducing process as for the X-ray paths for the chest including the metal piece, as described above; however, the X-ray CT apparatus 1 is configured to establish an ordinary set of paths as for the X-ray paths for the abdomen.

For example, when performing the scan on the subject described above, the X-ray CT apparatus 1 sets, as illustrated in the top section of FIG. 21, scan ranges R5 to R7 based on X-ray paths derived in accordance with the position of the metal piece included in the chest and a scan range R8 for the abdomen. In the present example, when the scan is to be performed by using a W-Volume scan having a constant scan range (e.g., having a width of 16 cm), there will be gaps between the scan range R5 and the scan range R6, as well as between the scan range R7 and the scan range R8, as illustrated in the top section of FIG. 21, and the data would be missing in those gaps.

To cope with this situation, the X-ray CT apparatus 1 according to the fourth embodiment is configured to be able to set a scan range to fill in the gaps. More specifically, the controlling function 37d re-establishes scan ranges so as to fill in the gaps between the scan ranges, on the basis of the manner in which the scan ranges overlap each other based on the X-ray paths derived in accordance with the processing effect of the metal artifact reducing process performed on the highly X-ray absorbent member. For example, as illustrated in the top section of FIG. 21, on a main scan planning screen, the display controlling function 37c arranges the scan ranges R5 to R8 set on the basis of the derived X-ray paths to be displayed in a position determining image.

In the present example, by referring to the position determining image, the operator sets scan ranges by operating the input circuitry 31 so that none of the CT image data from the main scan is missing. For example, as illustrated in the bottom section of FIG. 21, the operator moves the scan range R6 upward so as to overlap the scan range R5 and moves the scan range R7 downward so as to overlap the scan range R8. Further, as illustrated in the bottom section of FIG. 21, the operator fills in the gap between the scan ranges by setting another scan range R9 between the scan range R6 and the scan range R7. The controlling function 37d re-establishes the scan ranges R5 to R9 received via the input circuitry 31 as the scan ranges to be used in the main scan. By eliminating the gaps between the scan ranges in this manner, it is possible to prevent the missing of the data.

In the description above, the example is explained in which the operator sets the scan ranges; however, possible embodiments are not limited to this example. For instance, the controlling function 37d may set the scan ranges. In that situation, the controlling function 37d sets the scan ranges on the basis of the X-ray paths and the acquisition condition derived by the deriving function 37b and further judges whether there is any gap between the scan ranges. In this situation, when there are one or more gaps between the scan ranges, the controlling function 37d performs the operations of moving the already-set scan ranges and/or adding one or more new scan ranges. When it is possible to fill in the gaps by moving the scan ranges, the controlling function 37d may omit the operation of adding new scan ranges.

In the description above, the example is explained in which the scan is performed by using the W-Volume scan; however, possible embodiments are not limited to this example. For instance, it is acceptable to perform by scan by using a helical scan. In that situation, the controlling function 37d controls the moving speed of the couchtop 22 and the rotation speed of the rotating frame 15 so that there is no gap for the scan. In this situation, the controlling function 37d is able to exercise control while taking into consideration extra width allowances for the scanning during the helical scan. In other words, the controlling function 37d controls the moving speed of the couchtop 22 and the rotation speed of the rotating frame 15 so that the extra width allowances do not overlap in each rotation. With this arrangement, the X-ray CT apparatus 1 is able to keep exposure to X-rays at a minimum level.

Further, the X-ray CT apparatus 1 according to the fourth embodiment is also capable of generating and displaying a CT image suitable for an image interpretation process, from CT image data acquired at an angle corresponding to the derived X-ray paths. For example, the scan ranges R5 to R7 and R9 illustrated in the bottom section of FIG. 21 are positioned askew at an angle with respect to the body axis of the subject. Accordingly, the CT image data acquired by using the scan ranges is data askew at the angle. To cope with this situation, the X-ray CT apparatus 1 according to the fourth embodiment is configured to generate and display a CT image along a predetermined axis, from the CT image data acquired askew. For example, by controlling the image reconstructing circuitry 36, the display controlling function 37c generates the CT image on a coronal cross-sectional plane in which the body-axis direction in the image extends parallel to the vertical direction and further causes the display 32 to display the generated CT image. In one example, the image reconstructing circuitry 36 obtains information about the tilt angle and the slew angles of the gantry 10 and the couch device 20 and further generates a CT image by adjusting the angle from the CT image data while using the obtained information about the angles.

In the description above, the example is explained in which the X-ray paths are set by tilting the gantry 10 and the couch device 20 by the predetermined tilt angles and/or rotating the gantry 10 and the couch device 20 by the predetermined slew angle. Similarly to the situation where the scan ranges are positioned askew by controlling the gantry 10 and the couch device 20, the X-ray CT apparatus 1 is also capable of setting scan ranges and generating and displaying a CT image suitable for image interpretation processes even in the situation where the subject is positioned askew. In that situation, for example, the X-ray CT apparatus 1 causes the scan ranges to be displayed in a position determining image acquired while the subject is positioned askew, so as to receive settings of the scan ranges via the input circuitry 31. In one example, by operating the input circuitry 31, the operator is able to set the scan ranges so as to include a site positioned outside the scan ranges due to the subject being positioned askew. Further, in the X-ray CT apparatus 1, the controlling function 37d is also capable of setting scan ranges so as to include a site that is set in advance. Further, the display controlling function 37c is also capable of causing CT image data suitable for image interpretation processes to be generated from CT image data acquired askew due to the subject being positioned askew.

Figure 22A:
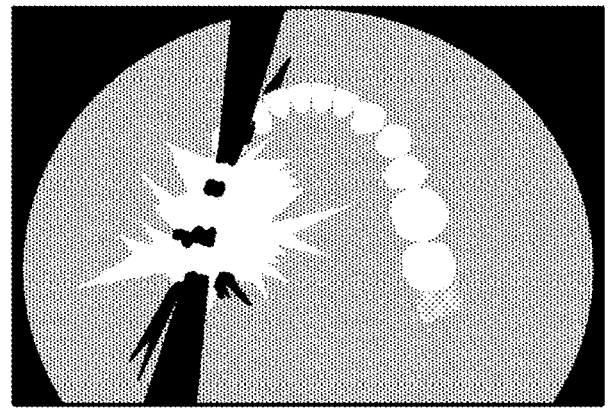
FIG. 22A is a drawing for explaining an example of a metal artifact reducing process according to the fourth embodiment.
Figure 22B:
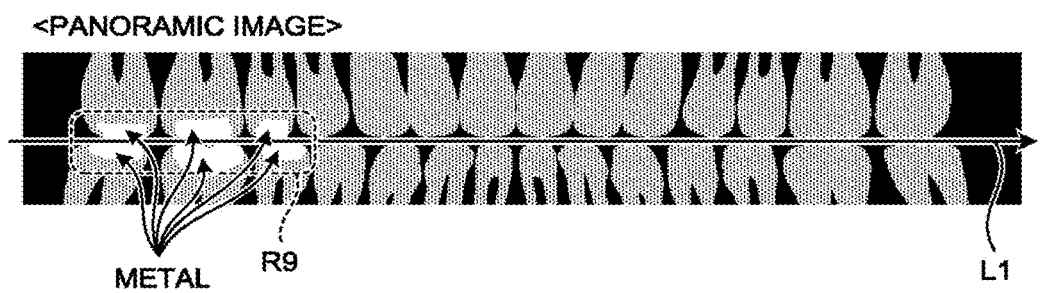
FIG. 22B is a drawing for explaining another example of the metal artifact reducing process according to the fourth embodiment.
Figure 22C:
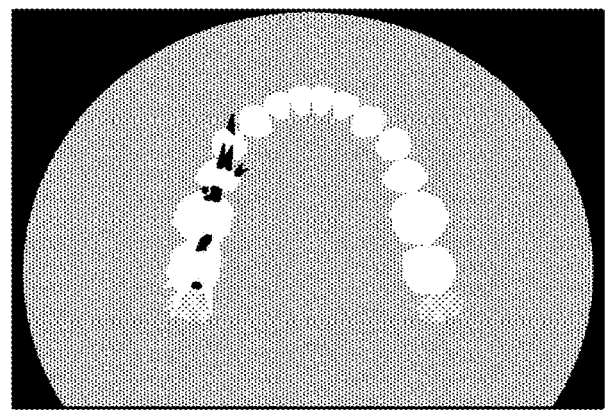
FIG. 22C is a drawing for explaining yet another example of the metal artifact reducing process according to the fourth embodiment.

Further, in the embodiments described above, the example is explained in which the paths are set while regarding the plurality of metal pieces as separate metal pieces; however, possible embodiments are not limited to this example. For instance, it is also acceptable to perform the process while regarding two or more metal pieces positioned adjacent to one another as a single metal piece. FIGS. 22A to 22C are drawings for explaining an example of a metal artifact reducing process according to the fourth embodiment.

For example, when a metal artifact reducing process is performed on the intraoral metal pieces placed on six teeth that are positioned close to one another, metal artifacts make a significant impact, as illustrated in FIG. 22A. It is because, due to the nature of the metal artifact reducing process, it may not be possible in some situations to achieve a high processing effect when the metal pieces are positioned close to each other. To cope with these situations, the deriving function 37b according to the fourth embodiment is configured to derive paths while regarding the plurality of metal pieces positioned close to one another as a single metal piece. For example, the deriving function 37b derives the paths while regarding the six metal pieces as a single metal piece, as illustrated in FIG. 22B. In other words, in the example in FIG. 22B, while the region R1 is regarded as a single metal piece, the straight line L1 is derived as a set of X-ray paths.

When a metal artifact reducing process is performed on the projection data acquired by performing the main scan, the image reconstructing circuitry 36 performs an interpolating process while regarding the region R9 as a single metal piece. With this arrangement, for example, it is possible to obtain a CT image in which the metal artifacts are reduced to a certain extent, as illustrated in FIG. 22C. In this situation, the X-ray CT apparatus 1 according to the fourth embodiment is also capable of performing the process without regarding the plurality of metal pieces positioned close to one another as a single metal piece. More specifically, when the degree of proximity (being positioned close) among the plurality of metal pieces is high, the plurality of metal pieces may be rendered as a single lump in acquired projection data. In that situation, it is possible to perform the same process without taking the trouble of regarding the region (the region R9 in FIG. 22B) containing the plurality of metal pieces as a single metal piece. In other words, the deriving function 37b judges whether or not it is necessary to regard the plurality of metal pieces as a single metal piece, on the basis of the state of the plurality of metal pieces in the projection data. For example, when the plurality of metal pieces in the projection data are rendered as a single lump, the deriving function 37b derives a set of X-ray paths for the single lump.

In consideration of a burden imposed on the subject, it is also acceptable to set priority levels among the control exercised on the X-ray paths by using the tilting and the slewing operations of the gantry 10, the control exercised by using the slewing operation of the couch device 20, and the control exercised on the paths realized by changing the posture of the subject that are described in the embodiments above. For example, the controlling function 37d may set the priority levels so as to control the gantry 10, the couch device 20, and the subject in the stated order, so as to set the X-ray paths derived by the deriving function 37b. In one example, the controlling function 37d first controls the tilting mechanism and the slewing mechanism of the gantry 10 for the purpose of realizing the X-ray paths derived by the deriving function 37b. When it is found impossible to set the paths even by controlling the gantry 10, the controlling function 37d controls the couch device 20 subsequently. When it is found impossible to set the paths even by controlling the couch device 20, the controlling function 37d presents information indicating that the posture of the subject needs to be changed.

Further, the constituent elements of the apparatuses and the devices illustrated in the drawings in the first embodiment are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

Further, it is possible to realize the controlling method explained in the first embodiment, by causing a computer such as a personal computer or a workstation to execute a control computer program (hereinafter, "control program") prepared in advance. It is possible to distribute the control program via a network such as the Internet. Further, the control program may be executed as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

As explained above, according to at least one aspect of the embodiments, it is possible to further reduce the metal artifacts.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
processing circuitry configured to:
    detect X-rays that have passed through a subject by using a detector and acquire projection data based on a detection result;
    obtain position information of a particular highly X-ray absorbent member in a body of the subject; and
    derive information about transmission paths of the X-rays in accordance with a processing effect of an artifact reducing process performed on the particular highly X-ray absorbent member, based on the position information of the particular highly X-ray absorbent member.

2. The X-ray CT apparatus according to claim 1, wherein the processing circuitry is further configured to:
    obtain position information of a plurality of highly X-ray absorbent members, including the particular highly X-ray absorbent member, in the body of the subject; and
    derive the information about the transmission paths of the X-rays, based on a distance between the plurality of highly X-ray absorbent members positioned on the transmission paths of the X-rays.

3. The X-ray CT apparatus according to claim 1, wherein the processing circuitry is further configured to derive the information about the transmission paths of the X-rays, in such a manner that the artifact reducing process is able to reduce artifacts in a region of interest within image data reconstructed from the projection data.

4. The X-ray CT apparatus according to claim 1, wherein the processing circuitry is further configured to:
    obtain position information of a plurality of highly X-ray absorbent members, including the particular highly X-ray absorbent member, in the body of the subject; and
    derive the information about the transmission paths of the X-rays that keep a quantity of highly X-ray absorbent members of the plurality of highly X-ray absorbent members positioned on the transmission paths of the X-rays one or smaller, or that minimize the quantity of highly X-ray absorbent members.

5. The X-ray CT apparatus according to claim 1, wherein the processing circuitry is configured to:
obtain position information of a plurality of highly X-ray absorbent members, including the particular highly X-ray absorbent member, in the body of the subject; and
derive the information about the transmission paths of the X-rays that maximize a distance between the plurality of highly X-ray absorbent members positioned on the transmission paths of the X-rays.

6. The X-ray CT apparatus according to claim 1, wherein the processing circuitry is further configured to:
obtain position information of a plurality of highly X-ray absorbent members, including the particular highly X-ray absorbent member, in the body of the subject; and
derive the information about the transmission paths of the X-rays obtained by eliminating, from previous information about previous transmission paths of X-rays, at least a most highly X-ray absorbent member among the plurality of highly X-ray absorbent members in the body of the subject.

7. The X-ray CT apparatus according to claim 1, wherein the processing circuitry is further configured to receive an operation to designate a predetermined region of the subject, and
the processing circuitry is further configured to derive the information about the transmission paths of the X-rays obtained by eliminating, from previous information about previous transmission paths of X-rays, the designated predetermined region.

8. The X-ray CT apparatus according to claim 7, wherein the processing circuitry is further configured to receive, as the predetermined region, one of a region indicating a metal artifact within a position determining image acquired from the subject, a region indicating the particular highly X-ray absorbent member within a position determining image, and a tooth region of the subject designated by using a dental system.

9. The X-ray CT apparatus according to claim 8, wherein the dental system includes one of a Zsigmondy system, an ADA system, and an FDI system.

10. The X-ray CT apparatus according to claim 1, wherein the processing circuitry is further configured to set an acquisition condition for acquiring the projection data, based on the information about the transmission paths of the X-rays, and
the processing circuitry is further configured to acquire the projection data by using the set acquisition condition.

11. The X-ray CT apparatus according to claim 10, wherein the acquisition condition is at least one of a tilt angle of a gantry including an X-ray source, a rotation angle of the gantry, and a rotation angle of a couch on which the subject is lying.

12. The X-ray CT apparatus according to claim 1, further comprising a light projector configured to irradiate a body surface of the subject with light of which an irradiation position is variable, wherein
the processing circuitry is further configured to control the light projector so as to project the light to a position on a body surface of the subject corresponding to the information about the transmission paths of the X-rays.

13. The X-ray CT apparatus according to claim 1, further comprising a display to display the information about the transmission paths of the X-rays, wherein as the information about the transmission paths of the X-rays, the processing circuitry is further configured to cause the display to display at least one of a position determining image indicating the information about the transmission paths of the X-rays, image information indicating a posture of the subject used for setting the information about the transmission paths of the X-rays in accordance with the processing effect of the artifact reducing process performed on the particular highly X-ray absorbent member, and a simulation image corresponding to when an acquiring process is performed by setting the information about the transmission paths of the X-rays in accordance with the processing effect of the artifact reducing process performed on the particular highly X-ray absorbent member.

14. The X-ray CT apparatus according to claim 1, wherein the processing circuitry is further configured to obtain the position information of the particular highly X-ray absorbent member in the body of the subject, based on a CT value of a position determining image of the subject.

15. The X-ray CT apparatus according to claim 1, wherein the processing circuitry is further configured to
obtain position information of a plurality of highly X-ray absorbent members including the particular highly X-ray absorbent member in the body of the subject; and
derive the information about the transmission paths of the X-rays while regarding the plurality of highly X-ray absorbent members that are positioned close to each other in the body of the subject as a single highly X-ray absorbent member.

16. The X-ray CT apparatus according to claim 1, further comprising an aiding tool configured to change a posture of the subject, for setting the information about the transmission paths of the X-rays in accordance with the processing effect of the artifact reducing process performed on the particular highly X-ray absorbent member.

17. The X-ray CT apparatus according to claim 1, wherein to perform an image taking process on a head of the subject, when the particular highly X-ray absorbent member is placed in a tooth part of the subject, the processing circuitry is further configured to select a mouthpiece used for eliminating the particular highly X-ray absorbent member from previous information about previous transmission paths of X-rays, based on the information about the transmission paths of the X-rays.

18. The X-ray CT apparatus according to claim 1, wherein the processing circuitry is further configured to cause a display to display a medical image based on projection data acquired based on the information about the transmission paths of the X-rays, as well as an acquisition condition of the projection data.

19. The X-ray CT apparatus according to claim 1, wherein, based on a manner in which scan ranges overlap each other based on the information about the transmission paths of the X-rays in accordance with the processing effect of the artifact reducing process performed on the particular highly X-ray absorbent member, the processing circuitry is further configured to re-establish the scan ranges so as to fill in a gap between the scan ranges.

20. The X-ray CT apparatus according to claim 1, wherein the processing circuitry is further configured to set an acquisition condition of the projection data in accordance with a posture of the subject that was changed for setting the information about the transmission paths of the X-rays in accordance with the processing effect of the artifact reducing process performed on the particular highly X-ray absorbent member.

* * * * *